United States Patent [19]

Sato et al.

[11] Patent Number: 4,621,046
[45] Date of Patent: Nov. 4, 1986

[54] PYRAZOLO(1,5-B)-1,2,4-TRIAZOLE DERIVATIVES

[75] Inventors: Tadahisa Sato; Toshio Kawagishi; Nobuo Furutachi, all of Kanagawa, Japan

[73] Assignee: Fuji Photo Film Co., Ltd., Kanagawa, Japan

[21] Appl. No.: 702,691

[22] Filed: Feb. 19, 1985

Related U.S. Application Data

[63] Continuation-in-part of Ser. No. 590,818, Mar. 19, 1984, Pat. No. 4,540,654.

[30] Foreign Application Priority Data

Mar. 18, 1983 [JP] Japan .................. 58-45512
Feb. 16, 1984 [JP] Japan .................. 59-27745

[51] Int. Cl.$^4$ ............... C07D 257/04; C07D 257/10; C07D 403/04; C07D 487/02
[52] U.S. Cl. ........................ 430/381; 534/752; 548/210; 548/215; 548/221; 548/251; 548/263; 548/266
[58] Field of Search ............... 548/266, 215, 221, 210, 548/263, 251; 534/752; 430/381

[56] References Cited

U.S. PATENT DOCUMENTS

| | | | |
|---|---|---|---|
| 3,598,602 | 8/1970 | Chapman | 534/752 |
| 3,705,896 | 12/1972 | Bailey et al. | 548/263 |
| 3,758,309 | 9/1973 | Bailey et al. | 548/263 X |
| 3,907,799 | 9/1975 | O'Brien et al. | 534/752 X |
| 4,007,276 | 2/1977 | Sale et al. | 548/263 X |
| 4,076,823 | 2/1978 | Wade et al. | 548/266 X |
| 4,119,635 | 10/1978 | Omodei-Sale et al. | 548/266 X |
| 4,150,139 | 4/1979 | Kuwada et al. | 548/263 X |
| 4,408,049 | 10/1983 | Gall | 548/263 X |
| 4,518,598 | 5/1985 | Hayes et al. | 548/266 X |
| 4,536,508 | 8/1985 | Clitherow et al. | 548/266 X |
| 4,540,654 | 9/1985 | Sato et al. | 430/381 |

FOREIGN PATENT DOCUMENTS

| | | | |
|---|---|---|---|
| 0119860 | 9/1984 | European Pat. Off. | 548/266 |
| 1334515 | 10/1970 | United Kingdom | 548/263 |
| 1340191 | 12/1973 | United Kingdom | 548/266 |
| 1458528 | 12/1976 | United Kingdom | 548/266 |

OTHER PUBLICATIONS

Research Disclosure #24531, Sep. 1984, No. 245, pp. 442–454, Disclosed Anonymously.

*Primary Examiner*—John E. Kittle
*Assistant Examiner*—Mukund J. Shah
*Attorney, Agent, or Firm*—Sughrue, Mion, Zinn, Macpeak, and Seas

[57] ABSTRACT

A novel pyrazolo[1,5-b]-1,2,4-triazole derivative represented by the general formula (I) is described.

$$\begin{array}{c} \text{N} - \text{N} \diagdown \text{N} \\ \text{R}_1 \diagdown \quad \diagup \text{R}_2 \\ \text{X} \quad \text{Y} \end{array} \quad (I)$$

wherein $R_1$ and $R_2$ which may be the same or different, each represents a hydrogen atom or a substituent; X represents a hydrogen atom or a group capable of being released upon coupling; and Y represents a hydrogen atom or an aralkyl group.

8 Claims, 1 Drawing Figure

PYRAZOLO(1,5-B)-1,2,4-TRIAZOLE DERIVATIVES

CROSS REFERENCE TO RELATED APPLICATION

This is continuation-in-part application of Ser. No. 590,818 filed Mar. 19, 1984, now U.S. Pat. No. 4,540,654.

FIELD OF THE INVENTION

The present invention relates to novel pyrazolo[1,5-b]-1,2,4-triazole derivatives.

BACKGROUND OF THE INVENTION

It is well known that an oxidized aromatic primary amine color developing agent formed by oxidation with exposed silver halide reacts with a coupler to form a dye such as an indophenol, an indoaniline, indamine, an azomethine, a phenoxazine, a phenazine and the like, thus forming a color image.

In order to form a magenta color image, a 5-pyrazolone type coupler, a cyanoacetophenone type coupler, an indazolone type coupler, a pyrazolobenzimidazole type coupler or a pyrazolotriazole type coupler is employed.

Magenta color image forming couplers which have been widely used in practice and on which various investigations have been made are generally 5-pyrazolones. It is known that dyes formed from 5-pyrazolone type couplers are excellent in fastness to heat and light but they have the undesirable absorption of yellow in the region around 430 nm which causes color turbidity.

In order to reduce the yellow component, a pyrazolobenzimidazole nucleus as described in British Pat. No. 1,047,612, an indazolone nucleus as described in U.S. Pat. No. 3,770,447 and a pyrazolotriazole nucleus as described in U.S. Pat. No. 3,725,067 have been proposed as a magenta color image forming coupler skeleton. However, the magenta couplers described in these patents are still insufficient since they provide only poor color images when they are mixed with a silver halide emulsion in the form of a dispersion in a hydrophilic protective colloid such as gelatin, they have a low solubility in an organic solvent having a high boiling point, they have some difficulties in synthesis thereof, or they have a relatively low coupling activity in conventional developing solutions.

The present inventors have carried out extensive investigations on a novel magenta color image forming couplers free from the subsidiary absorptions in the region around 430 nm which is the most disadvantageous point in view of spectral absorption characteristics of a dye formed from 5-pyrazolone type magenta couplers. As a result, the present inventors have found novel pyrazolo[1,5-b]-1,2,4-triazole derivative which can be used as a coupler to provide a color image without a subsidiary absorption in a shorter wavelength side of the main absorption and which have good fastness and which can be easily synthesized.

SUMMARY OF THE INVENTION

Therefore, an object of the present invention is to provide a novel pyrazolo[1,5-b]-1,2,4-triazole derivative represented by the general formula (I) which can be used as a magenta color image forming coupler having an excellent color reproducibility, color forming rate and maximum color density, which are advantageous with respect to their synthesis and which can prepare the so-called 2-equivalent couplers by introducing a releasing group into their coupling active sites whereby the amount of silver needed can be reduced.

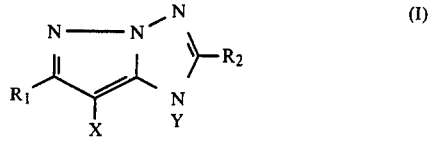

wherein $R_1$ and $R_2$, which may be the same or different, each represents a hydrogen atom or a substituent; X represents a hydrogen atom or a group capable of being released upon coupling; and Y represents a hydrogen atom or an aralkyl group.

BRIEF DESCRIPTION OF THE ACCOMPANYING DRAWING

FIG. 1 is a graph showing the absorption spectra of dyes formed from Comparison Compound A (Curve A) and Compound (1) according to the present invention (Curve B) in the manner as described in Reference Example 1, respectively.

DETAILED DESCRIPTION OF THE INVENTION

Figure 1:
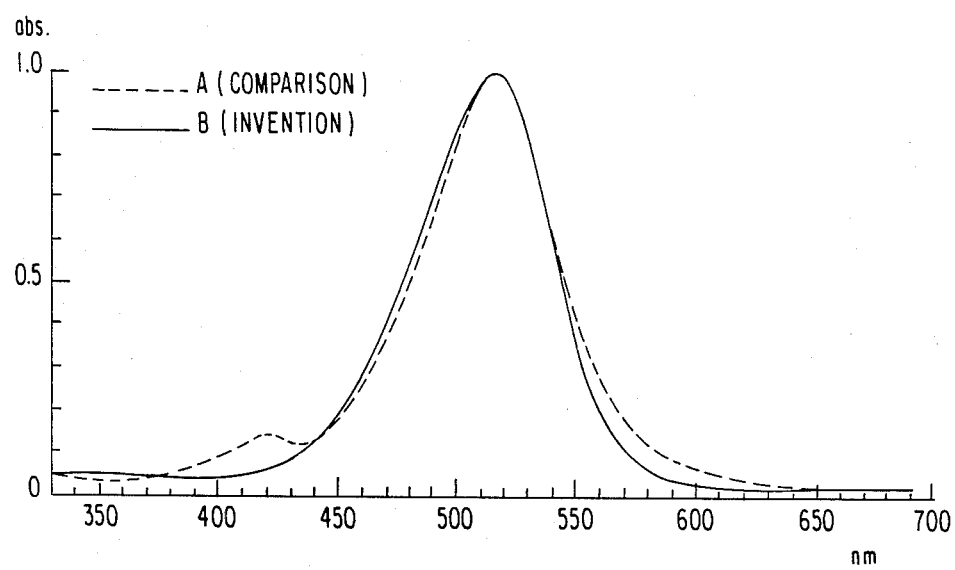

In the above-described general formula (I), $R_1$ and $R_2$ each preferably represents a hydrogen atom, a halogen atom, an aliphatic residue, an aryl group, a heterocyclic group, a cyano group, an alkoxy group, an aryloxy group, an acylamino group, an anilino group, a ureido group, a sulfamoylamino group, an alkylthio group, an arylthio group, an alkoxycarbonylamino group, a sulfonamido group, a carbamoyl group, a sulfamoyl group, a sulfonyl group, a heterocyclicoxy group, an acyloxy group, a carbamoyloxy group, a silyloxy group, an aryloxycarbonylamino group, an imido group, a heterocyclicthio group, a sulfinyl group, a phosphonyl group, an aryloxycarbonyl group, an acyl group or an alkoxycarbonyl group; X preferably represents a hydrogen atom, a halogen atom, a carboxy group or a group capable of being released upon coupling which is bonded to the carbon atom of the coupling position through an oxygen atom, a nitrogen atom, a carbon atom or a sulfur atom; and Y preferably represents a hydrogen atom or a benzyl group. Further, $R_1$, $R_2$ or X may be a divalent group to form a bis coupler.

In more detail, $R_1$ and $Rhd 2$ each represents a hydrogen atom; a halogen atom (for example, a chlorine atom, a bromine atom, etc.); an aliphatic residue including a straight chain or branched chain alkyl group having from 1 to 32 carbon atoms, an aralkyl group, an alkenyl group, an alkinyl group, a cycloalkyl group and a cycloalkenyl group, which may be substituted with a substituent bonded through an oxygen atom, a nitrogen atom, a sulfur atom or a carbonyl group, a hydroxy group, an amino group, a nitro group, a carboxy group, a cyano group or a halogen atom (for example, a methyl group, a propyl group, a t-butyl group, a trifluoromethyl group, a tridecyl group, a 2-methanesulfonylethyl group, a 3-(3-pentadecylphenoxy)propyl group, a 3-{4-{2-[4-(4-hydroxyphenylsulfonyl)phenoxy]dodecaneamido}phenyl}propyl group, a 2-ethoxytridecyl group, a trifluoromethyl group, a cyclopentyl group, a 3-(2,4-di-t-amylphenoxy)propyl group, etc.); an aryl group (for example, a phenyl group, a 4-t-butylphenyl group, a 2,4-di-t-amylphenyl group, a 4-tetradecanamidophenyl group, etc.); a heterocyclic group (for example, a 2-furyl group, a 2-thienyl group, a 2-pyrimidinyl group, a 2-benzothiazolyl group, etc.); a cyano group; an alkoxy group (for example, a methoxy group, an ethoxy group, a 2-methoxyethoxy group, a 2-dodecylethoxy group, a 2-methanesulfonylethoxy group, etc.); an aryloxy group (for example, a phenoxy group, a 2-methylphenoxy group, a 4-t-butylphenoxy group, etc.); an acylamino group (for example, an acetamido group, a benzamido group, a tetradecanamido group, an α-(2,4-di-t-amylphenoxy)butyramido group, a γ-(3-t-butyl-4-hydroxyphenoxy)butyramido group, an α-[4-(4-hydroxyphenylsulfonyl)phenoxy]decanamido group, etc.); an anilino group (for example, a phenylamino group, a 2-chloroanilino group, a 2-chloro-5-tetradecanamidoanilino group, a 2-chloro-5-dodecyloxycarbonylanilino group, an N-acetylanilino group, a 2-chloro-5-[α-(3-t-butyl-4-hydroxyphenoxy)-dodecanamido]anilino group, etc.); a ureido group (for example, a phenylureido group, a methylureido group, an N,N-dibutylureido group, etc.); a sulfamoylamino group (for example, an N,N-dipropylsulfamoylamino group, an N-methyl-N-decylsulfamoylamino group, etc.); an alkylthio group (for example, a methylthio group, an octylthio group, a tetradecylthio group, a 2-phenoxyethylthio group, a 3-phenoxypropylthio group, a 3-(4-t-butylphenoxy)propylthio group, etc.); an arylthio group (for example, a phenylthio group, a 2-butoxy-5-t-octylphenylthio group, a 3-pentadecylphenylthio group, a 2-carboxyphenylthio group, a 4-tetradecanamidophenylthio group, etc.); an alkoxycarbonylamino group (for example, a methoxycarbonylamino group, a tetradecyloxycarbonylamino group, etc.); a sulfonamido group (for example, a methanesulfonamido group, a hexadecanesulfonamido group, a benzenesulfonamido group, a p-toluenesulfonamido group, an octadecanesulfonamido group, a 2-methyloxy-5-t-butylbenzenesulfonamido group, etc.); a carbamoyl group (for example, an N-ethylcarbamoyl group, an N,N-dibutylcarbamoyl group, an N-(2-dodecyloxyethyl)carbamoyl group, an N-methyl-N-dodecylcarbamoyl group, an N-[3-(2,4-di-t-amylphenoxy)propyl]carbamoyl group, etc.); a sulfamoyl group (for example, an N-ethylsulfamoyl group, an N,N-dipropylsulfamoyl group, an N-(2-dodecyloxyethyl)sulfamoyl group, an N-ethyl-N-dodecylsulfamoyl group, an N,N-diethylsulfamoyl group, etc.); a sulfonyl group (for example, a methanesulfonyl group, an octanesulfonyl group, a benzenesulfonyl group, a toluenesulfonyl group, etc.); an alkoxycarbonyl group (for example, a methoxycarbonyl group, a butyloxycarbonyl group, a dodecyloxycarbonyl group, an octadecyloxycarbonyl group, etc.); a heterocyclicoxy group (for example, a 1-phenyltetrazole-5-oxy group, 2-tetrahydropyranyloxy group, etc.); an acyloxy group (for example, an acetoxy group, etc.); a carbamoyloxy group (for example, an N-methylcarbamoyloxy group, an N-phenylcarbamoyloxy group, etc.); a silyloxy group (for example, a trimethylsilyloxy group, a dibutylmethylsilyloxy group, etc.); an aryloxycarbonylamino group (for example, a phenoxycarbonylamino group, etc.); an imido group (for example, an N-succinimido group, an N-phthalimido group, a 3-octadecenylsuccinimido group, etc.); a heterocyclicthio group (for example, a 2-benzothiazolylthio group, a 2,4-diphenoxy-1,3,5-triazole-6-thio group, a 2-pyridylthio group, etc.); a sulfinyl group (for example, a dodecanesulfinyl group, a 3-pentadecylphenylsulfinyl group, a 3-phenoxypropylsulfinyl group, etc.); a phosphonyl group (for example, a phenoxyphosphonyl group, an octyloxyphosphonyl group, a phenylphosphonyl group, etc.); an aryloxycarbonyl group (for example, a phenoxycarbonyl group, etc.); or an acyl group (for example, an acetyl group, a 3-phenylpropanoyl group, a benzoyl group, a 4-dodecyloxybenzoyl group, etc.). In the substituents $R_1$ and $R_2$, an alkyl group or an alkyl moiety contains 1 to 32 carbon atoms, and an aryl group or an aryl moiety contains 6 to 32 carbon atoms.

X represents a hydrogen atom; a halogen atom (for example, a chlorine atom, a bromine atom, an iodine atom, etc.); a carboxy group; a group bonded to the coupling position through an oxygen atom (for example, an acetoxy group, a propanoyloxy group, a benzoyloxy group, a 2,4-dichlorobenzoyloxy group, an ethoxyoxaloyloxy group, a pyruvyloxy group, a cinnamoyloxy group, a phenoxy group, a 4-cyanophenoxy group, a 4-methanesulfonamidophenoxy group, a 4-methanesulfonylphenoxy group, an α-naphthoxy group, a 3-pentadecylphenoxy group, a benzyloxycarbonyloxy group, an ethoxy group, a 2-cyanoethoxy group, a benzyloxy group, a 2-phenethyloxy group, a 2-phenoxyethoxy group, a 5-phenyltetrazolyloxy group, a 2-benzothiazolyloxy group, etc.); a group bonded to the coupling position through a nitrogen atom (for example, a benzenesulfonamido group, an N-ethyltoluenesulfonamido group, a pentafluorobutanamido group, a 2,3,4,5,6-pentafluorobenzamido group, an octanesulfonamido group, a p-cyanophenylureido group, an N,N-diethylsulfamoylamino group, a 1-piperidyl group, a 5,5-dimethyl-2,4-dioxo-3-oxazolidinyl group, a 1-benzyl-5-ethoxy-3-hydantoinyl group, a 2N-1,1-dioxo-3(2H)-oxo-1,2-benzisothiazolidin-2-yl group, a 2-oxy-1,2-dihydro-1-pyridinyl group, an imidazolyl group, a pyrazolyl group, a 3,5-diethyl-1,2,4-triazol-1-yl group, a 5- or 6-bromobenzotriazol-1-yl group, a 5-methyl-1,2,3,4-tetrazol-1-yl group, a benzimidazolyl group, a 4-methoxyphenylazo group, a 4-pivaloylaminophenylazo group, a 2-hydroxy-4-propanoylphenylazo group, etc.); a group bonded to the coupling position through a sulfur atom (for example, a phenylthio group, a 2-carboxyphenylthio group, a 2-methoxy-5-t-octylphenylthio group, a 4-methanesulfonylphenylthio group, a 4-octanesulfonamidophenylthio group, a benzylthio group, a 2-cyanoethylthio group, a 1-ethoxycarbonyltridecylthio group, a 5-phenyl-2,3,4,5-tetrazolylthio group, a 2-benzothiazolylthio group, a thiocyano group, an N,N-diethylthiocarbonylthio group, a dodecyloxythiocarbonylthio group, etc.); or a group bonded to the coupling position through a carbon atom (for example, a triphenylmethyl group, a hydroxymethyl group, an N-morpholinomethyl group, a group represented by the following formula:

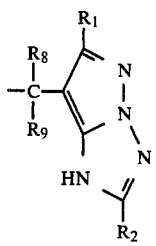

wherein $R_8$ and $R_9$ each represents a hydrogen atom, an alkyl group, an aryl group or a heterocyclic group; and $R_1$ and $R_2$ each has the same meaning as defined hereinbefore, etc.). In the substituents $R_8$ and $R_9$, an alkyl group contains 1 to 18 carbon atoms and an aryl group contains 6 to 18 carbon atoms.

The cases wherein $R_1$, $R_2$ or X represents a divalent group to form a bis coupler are described in more detail hereinafter. In such cases, $R_1$ and $R_2$ each represents a substituted or unsubstituted alkylene group (for example, a methylene group, an ethylene group, a 1,10—decylene group, $-CH_2CH_2-O-CH_2CH_2-$, etc.); a substituted or unsubstituted phenylene group (for example, a 1,4-phenylene group, a 1,3-phenylene group

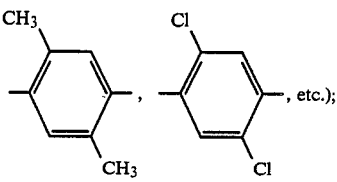

a group of the formula; $-NHCO-R_3-CONH-$ (wherein $R_3$ represents a substituted or unsubstituted alkylene group or a substituted or unsubstituted phenylene group) including, for example, $-NHCOCH_2CH_2CONH-$,

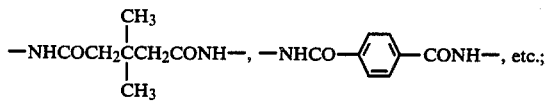

or a group of the formula: $-S-R_3-S-$ (wherein $R_3$ is the same meaning as defined above) including, for example, $-SCH_2CH_2S-$,

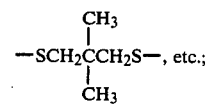

and X represents a divalent group appropriately formed from the monovalent group for X described above.

Of the compounds according to the present invention, the pyrazolo[1,5-b]-1,2,4-triazole compounds represented by the general formula (I') are particularly preferred.

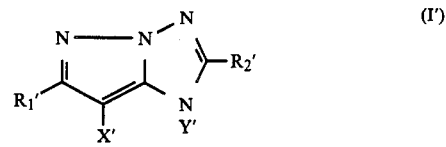

(I')

wherein $R_1'$ and $R_2'$ each independently represents a hydrogen atom, an alkyl group or a phenyl group; X' represents a hydrogen atom, a halogen atom, an acyl group, a nitroso group, an amino group, or a substituted amino group; and Y' represents a hydrogen atom or a benzyl group.

The alkyl group for $R_1'$ and $R_2'$ is preferably a straight chain or branched chain alkyl group having from 1 to 22 carbon atoms, for example, a methyl group, an ethyl group, a butyl group, a pentyl group, a hexyl group, a heptyl group, an octyl group, a decyl group, a tridecyl group, an octadecyl group, etc. The alkyl group and the phenyl group for $R_1'$ and $R_2'$ may be substituted with substituent(s) and, examples of the substituents can be referred to the substituents for the aliphatic residue and the aryl group for $R_1$ and $R_2$.

The halogen atom for X' is preferably a chlorine atom, a bromine atom or an iodine atom. The acyl group for X' is preferably an aliphatic acyl group or an aromatic acyl group, and examples thereof can be referred to the examples of the group bonded to the coupling position through an oxygen atom for X. The substituted amino group for X' may form a heterocyclic ring. Examples of the substituted amino group for X' can be referred to the examples of the group bonded to the coupling position through a nitrogen atom for X.

Specific examples of the representative pyrazolo[1,5-b]-1,2,4-triazole derivative according to the present invention are set forth below, but the present invention should not be construed as being limited thereto.

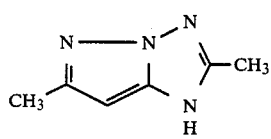 (1)

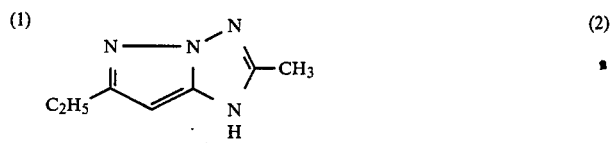 (2)

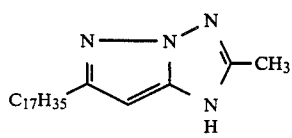 (3)

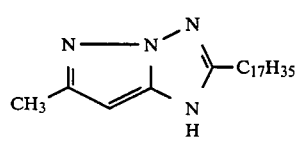 (4)

-continued
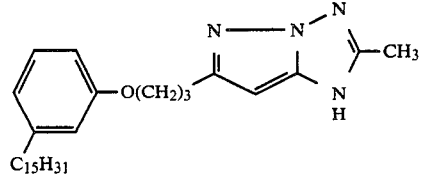 (5)
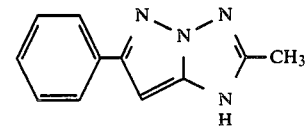 (6)
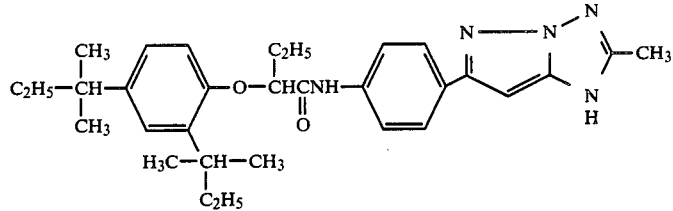 (7)
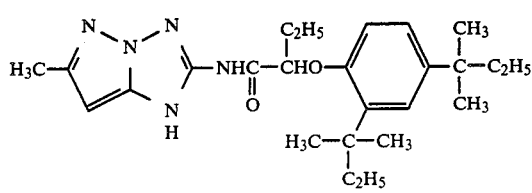 (8)
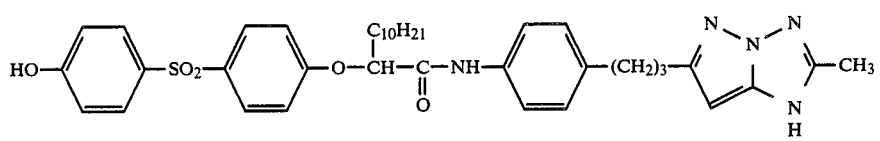 (9)
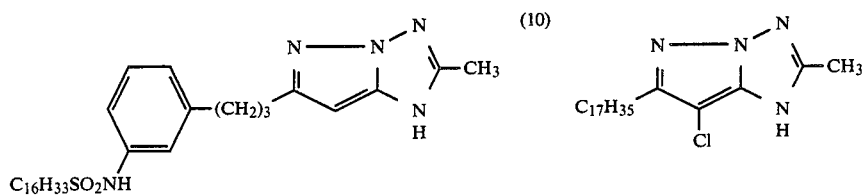 (10)
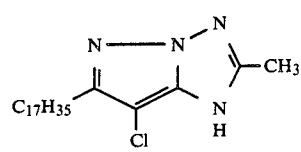 (11)
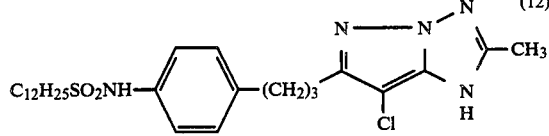 (12)
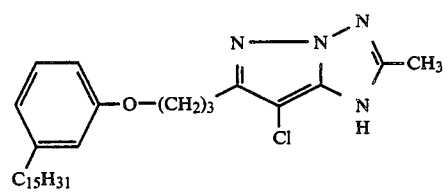 (13)
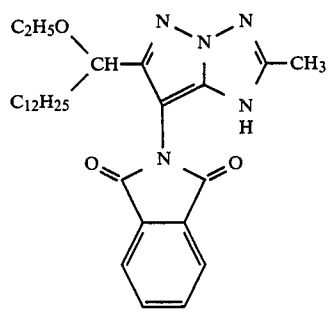 (14)
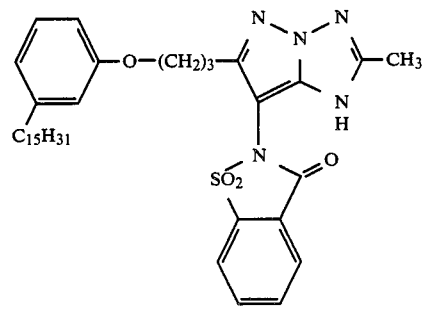 (15)
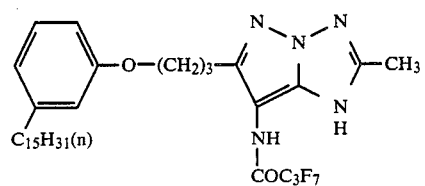 (16)
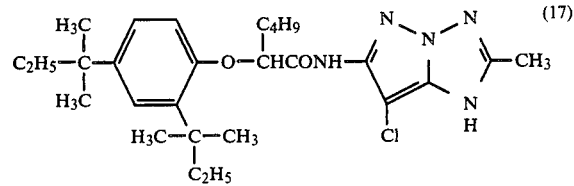 (17)

-continued
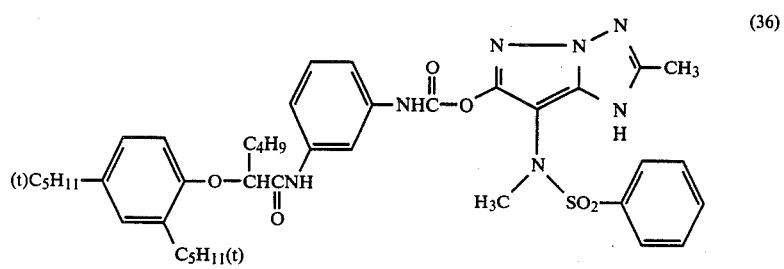 (36)
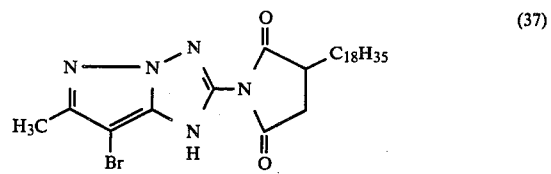 (37)
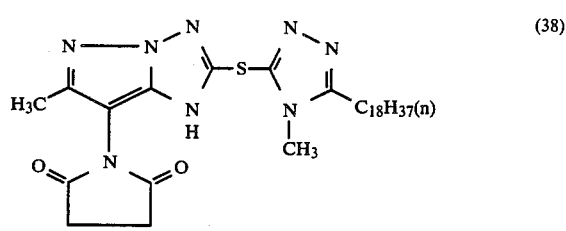 (38)
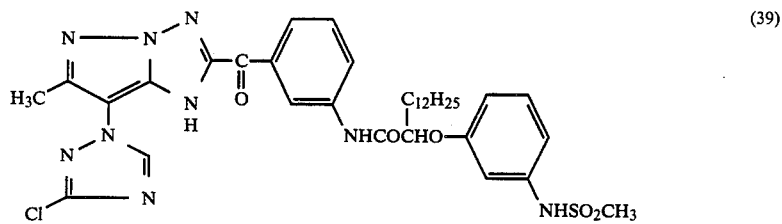 (39)
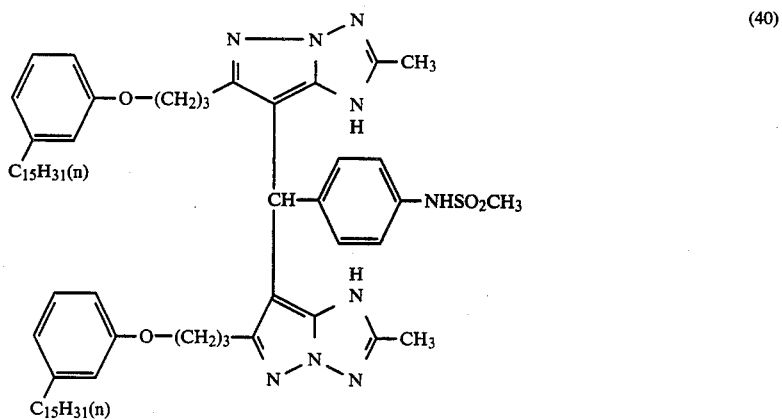 (40)
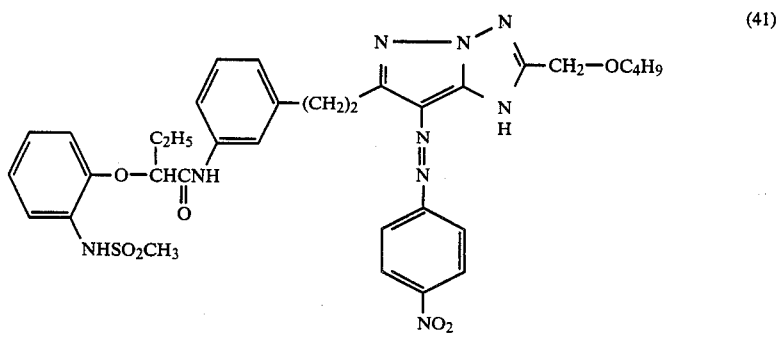 (41)

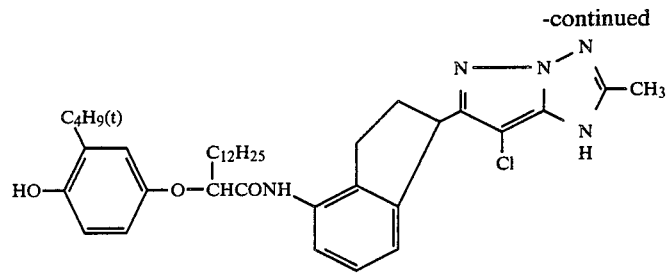
(42)
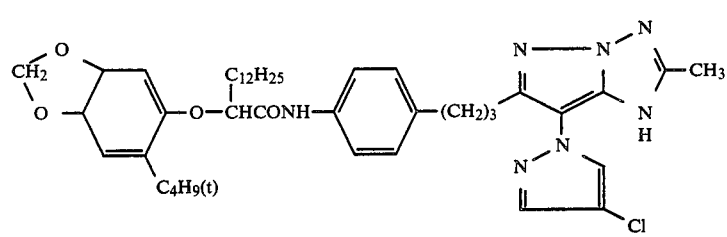
(43)
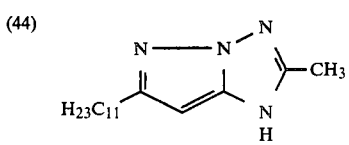
(44)
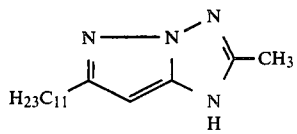
(45)
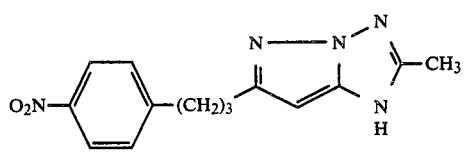
(46)
(47)
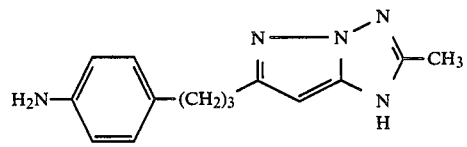
(48)
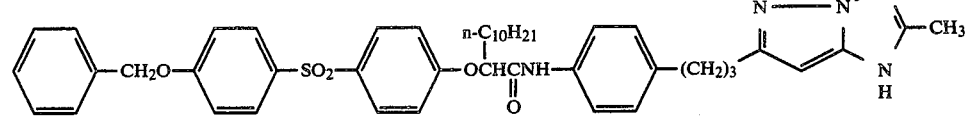
(49)
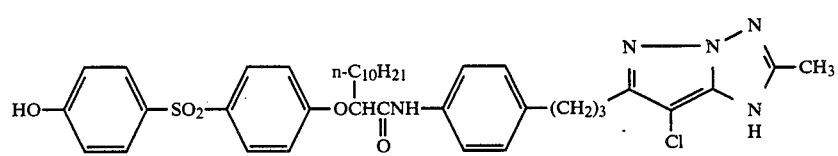
(50)
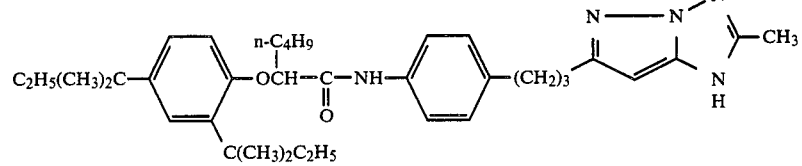
(51)
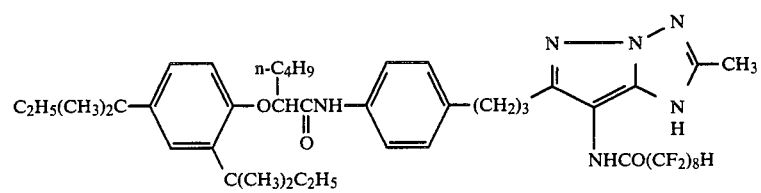
(52)

-continued
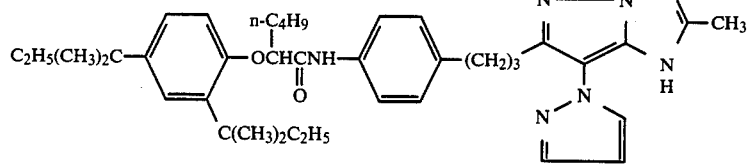 (53)
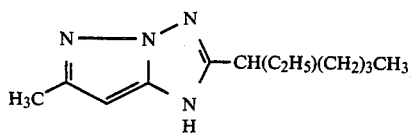 (54)
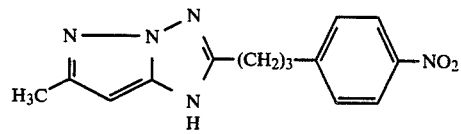 (55)
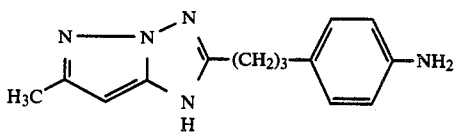 (56)
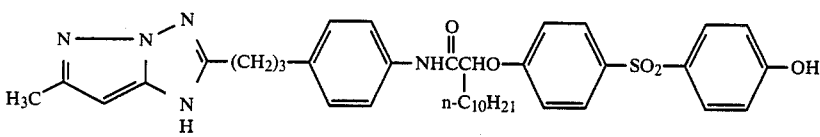 (57)
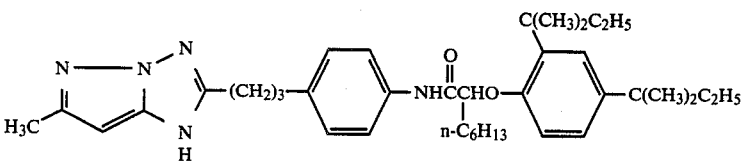 (58)
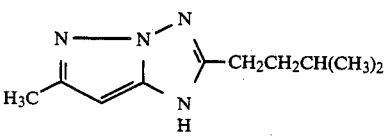 (59)
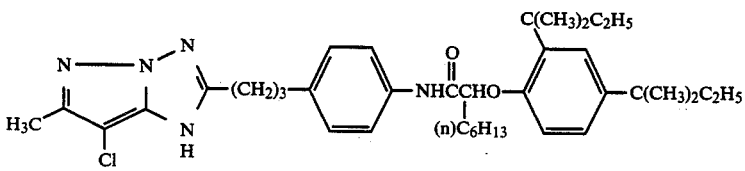 (60)
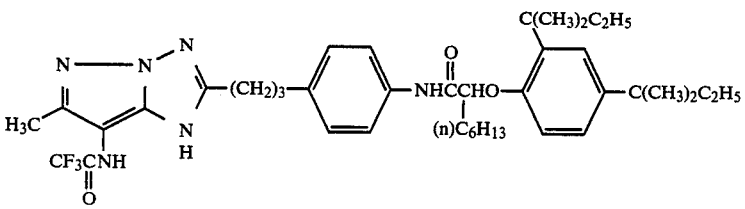 (61)
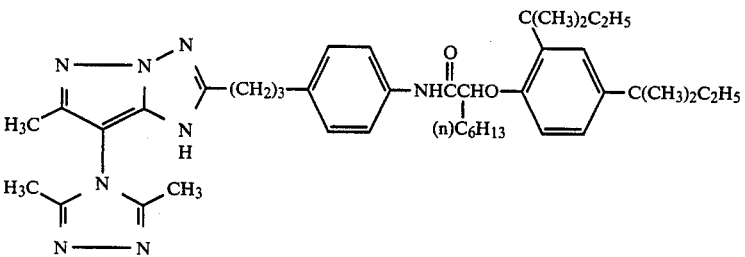 (62)

-continued
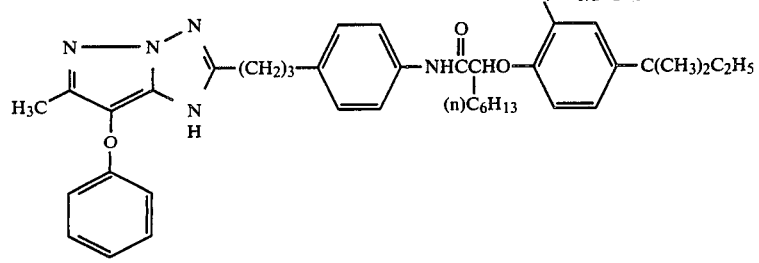 (63)
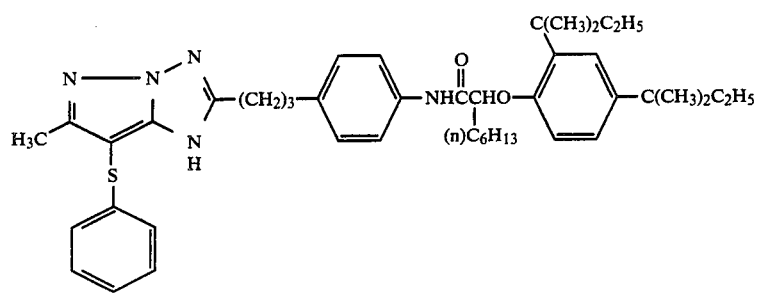 (64)
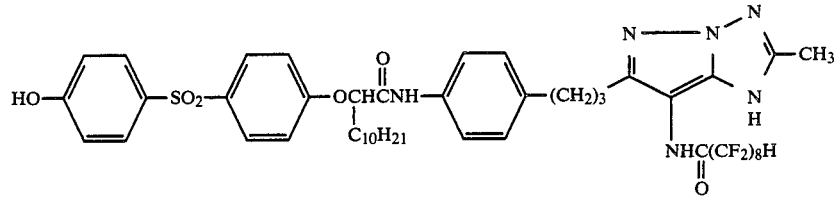 (65)
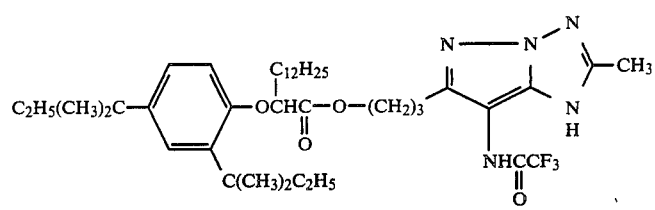 (66)
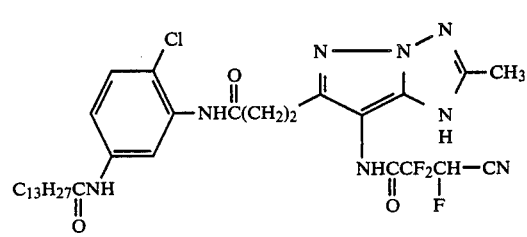 (67)
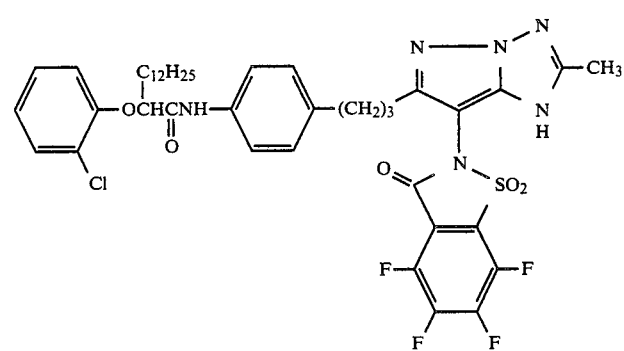 (68)

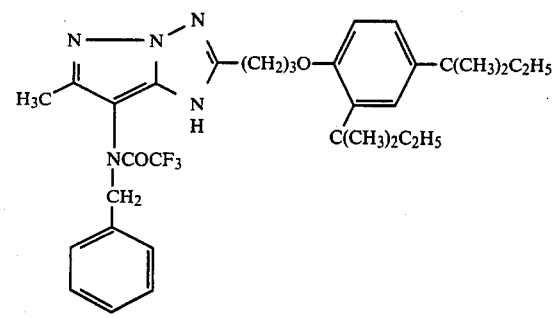
(69)
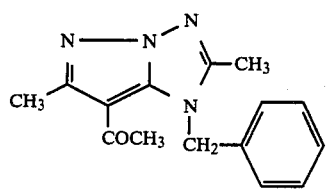
(70)
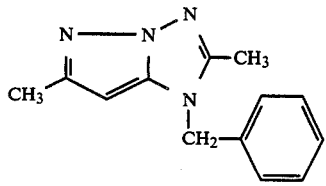
(71)
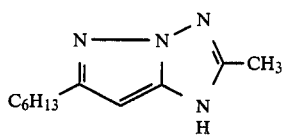
(72)
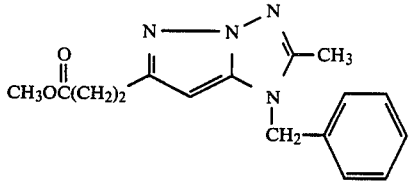
(73)
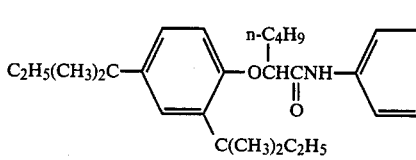
(74)
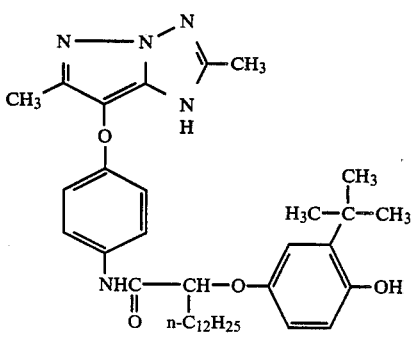
(75)
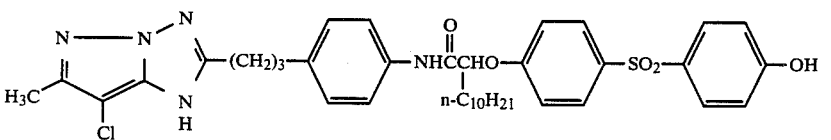
(76)
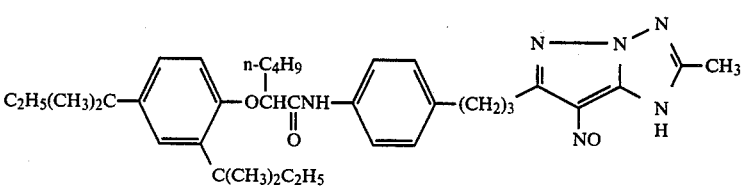
(77)

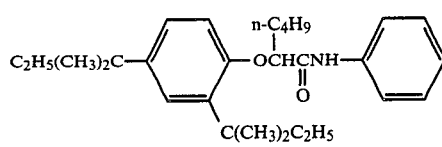
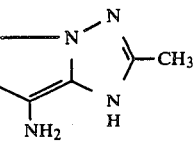(78)

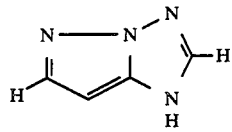(79)  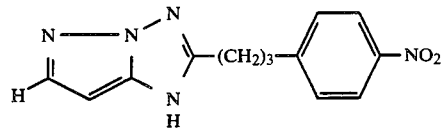(80)

The pyrazolo[1,5-b]-1,2,4-triazole derivative according to the present invention can be generally synthesized using any of six methods, reaction schemes of which are shown below.

Method I

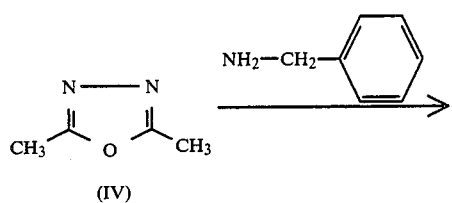
(IV)

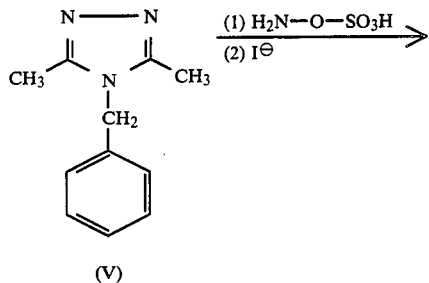
(V)

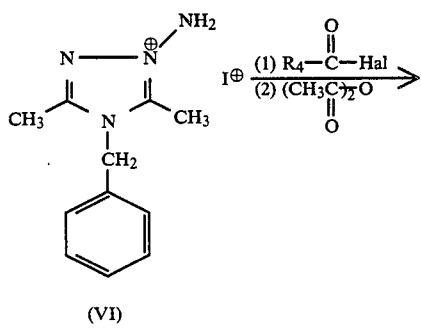
(VI)

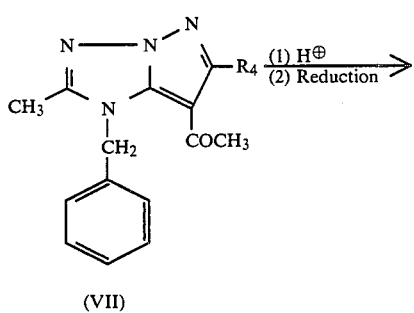
(VII)

-continued
Method I

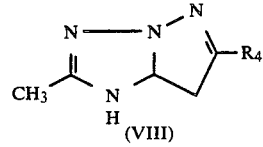
(VIII)

In the above formulae, $R_4$ represents an alkyl group, an aryl group or a heterocyclic group; and Hal represents a halogen atom.

The starting material of the formula (IV) can be synthesized by the method as described in Ber., Vol. 32, page 797 (1899).

Method II

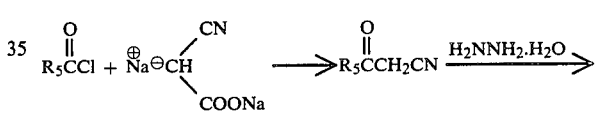

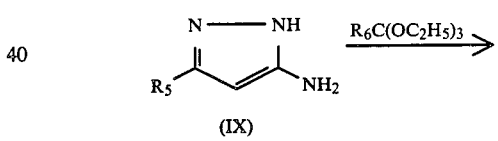
(IX)

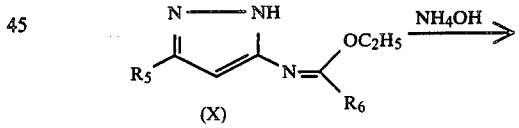
(X)

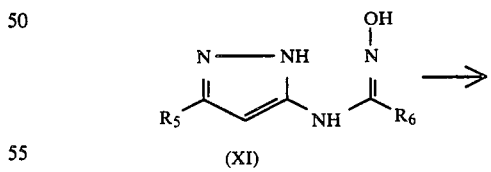
(XI)

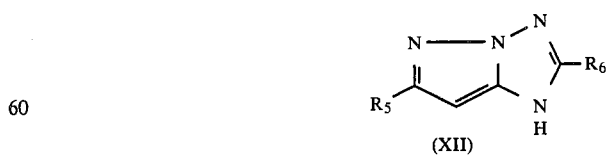
(XII)

The target compound in the structural formula of which $R_5$ and $R_6$ independently represent an alkyl group, an aryl group, or a heterocyclic group can be synthesized by following the scheme indicated above. Either of the groups, $R_5$ and $R_6$, may be substituted.

Specifically, where $R_5$ is methyl, the compound of (IX) can be readily obtained by reaction of 3-aminocrotonitrile with hydrazine. This method is characterized by producing the target compound by subjecting the reaction mixture to dehydrating cyclization condensation in the final stage of reaction.

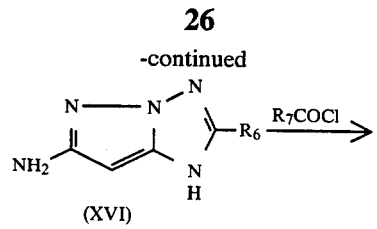

Method III

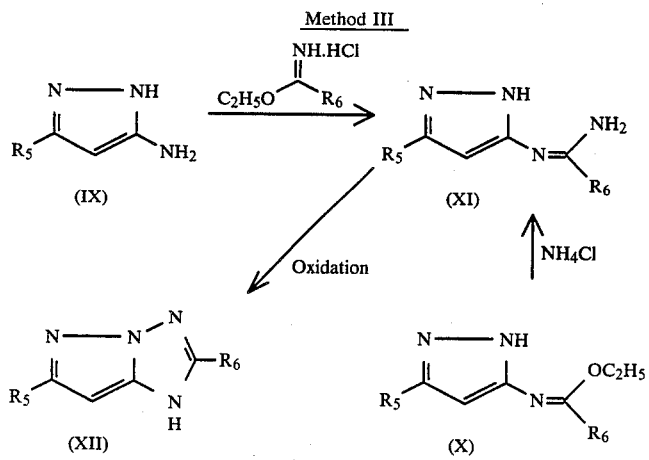

This method comprises obtaining the compound (XII) of this invention by subjecting to oxidative condensation the compound (XI) derived from either the intermediate of the Method II, i.e., 5-amino-3-substituted-pyrazole (IX), or the immediately ensuing intermediate (X). In the structural formulae of the compounds involved in this method, $R_5$ and $R_6$ independently represent an alkyl group, an aryl group, or a heterocyclic group. Either of the groups, $R_5$ and $R_6$, may be substituted.

Method IV

This method involves synthesis of a pyrazolotriazole of this invention having an amino group at the 6-position from 3,5-diaminopyrazole as the starting material by subjecting this starting material to dehydrating cyclization condensation by the procedure of the second method while keeping the amino group at the 3-position protected. A typical reaction scheme for this method is as follows.

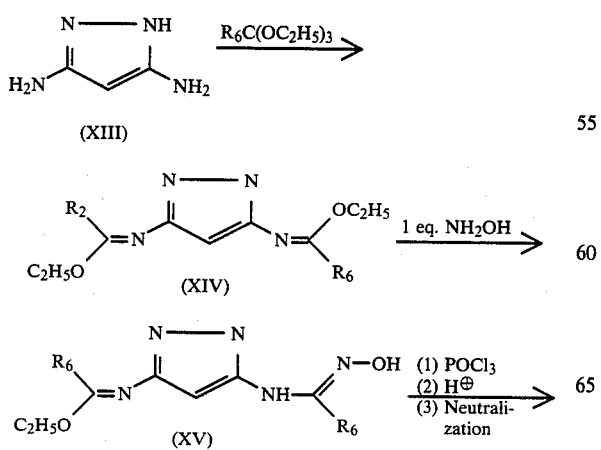

In the structural formulae indicated above, $R_6$ represents an alkyl, aryl, or heterocyclic group and $R_7$ represents an alkyl, aryl, heterocyclic, alkoxy, aryloxy, alkylamino, or arylamino group. $R_7SO_2Cl$ may be used in the place of $R_7COCl$. The aforementioned starting material (XIII) can be synthesized by the method disclosed in *J. Prakt. Chem.*, Vol. 320, page 533 (1978).

Method V

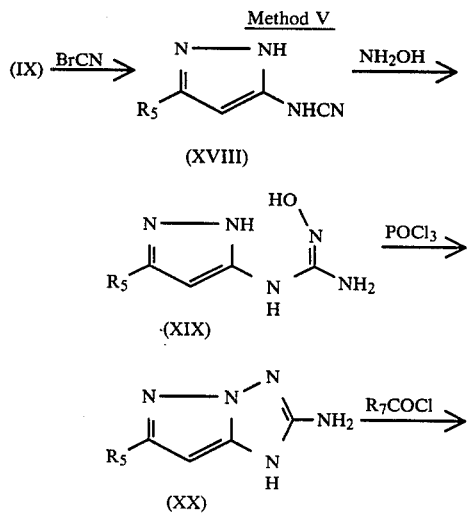

-continued

Method V

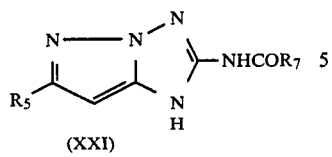

(XXI)

In the structural formulae indicated above, $R_5$ and $R_7$ independently represent any of the substituents indicated with respect to the structural formulae involved in the Method II and Method IV.

Method VI

Synthesis methods of polymer couplers are generally described below.

Polymer couplers can be synthesized by solution polymerization and emulsion polymerization. With respect to the solution polymerization the methods as described in U.S. Pat. No. 3,451,820 and Japanese Patent Application (OPI) No. 28745/83 can be utilized (the term "OPI" as used herein refers to a "published unexamined Japanese patent application"). More specifically, a monomer coupler containing a part represented by the general formula (I) and a non-color-forming ethylenic monomer (for example, an acrylic acid such as acrylic acid, α-chloroacrylic acid, methacrylic acid, etc.; and an ester or an amide derived from an acrylic acid such as acrylamine, n-butylacrylamide, n-butyl methacrylate, methyl methacrylate, ethyl methacrylate, etc.) are dissolved in or mixed with a soluble organic solvent (for example, dioxane, methyl cellosolve, etc.) in an appropriate ratio and polymerization is initiated at an appropriate temperature (in a range from about 30° C. to 100° C.) with a free radical which is formed by a physical action such as irradiation of ultraviolet rays, high energy radiations, etc., or a chemical action of an initiator such as a persulfate, hydrogen peroxide, benzoyl peroxide, an azobisalkyronitrile, etc. The polymer thus-synthesized is isolated by extraction with an organic solvent, concentration or pouring into water after the completion of the polymerization reaction. With respect to emulsion polymerization the method as described in U.S. Pat. No. 3,370,952 can be utilized.

General methods for introducing a group capable of being released upon coupling into a coupler are described in the following.

(1) Method for Connecting Oxygen Atom:

A 4-equivalent mother coupler according to the present invention, i.e., pyrazolo[1,5-b]-1,2,4-triazole type coupler, is converted to a dye according to the method as described in Example 1 hereinafter. The resulting dye is hydrolyzed in the presence of an acid catalyst to form a ketone body thereof. The ketone body is hydrogenated with a Pd-carbon catalyst, or reduced with Zn-acetic acid or with sodium borohydride to produce a 7-hydroxy-pyrazolo[1,5-b]-1,2,4-triazole. The resulting triazole is reacted with one of various kinds of halides to obtain the desired coupler which has an oxygen atom as the connecting atom to the coupling releasing group. For more detail the descriptions in U.S. Pat. No. 3,926,631 and Japanese Patent Application (OPI) No. 70817/82 can be referred to.

(2) Method for Connecting Nitrogen Atom:

Methods for connecting a nitrogen atom are broadly classified into three groups. A method belonging to the first group comprises introducing a nitroso group to the coupling active position of a coupler using an appropriate nitrosating agent, reducing the nitroso group by an appropriate method (for example, a hydrogenation method using Pd-carbon, etc., as a catalyst, a chemical reduction method using stannous chloride, etc., or so on) to convert to 7-amino-pyrazolo[1,5-b]-1,2,4-triazole, and reacting the resulting amino compound with one of various kinds of halide, as described in U.S. Pat. No. 3,419,391. According to this method, amido compounds are mainly synthesized.

A method belonging to the second group comprises halogenating the 7-position of a coupler using an appropriate halogenating agent, for example, sulfuryl chloride, chlorine gas, bromine, N-chlorosuccinimide, N-bromosuccinimide, etc., as described in U.S. Pat. No. 3,725,067, and then replacing the resulting halogen atom by a nitrogen-containing hetero ring in the presence of an appropriate base catalyst, for example, triethylamine, sodium hydroxide, diazabicyclo-[2,2,2]-octane, anhydrous potassium carbonate, etc., as described in Japanese Patent Publication No. 45135/81 to synthesize a coupler having a coupling releasing group connecting through a nitrogen atom at the 7-position thereof. According to this method couplers having a phenoxy group at the 7-position thereof which are compounds connecting through an oxygen atom can also be synthesized.

A method belonging to the third group is effective for the introduction of an aromatic nitrogen-containing hetero ring of 6π- or 10π-electron system to the 7-position of a coupler. This method comprises adding two or more moles of an aromatic nitrogen-containing hetero ring of 6π- or 10π-electron system to 1 mole of a 7-halogenated compound as prepared using the method described in the above second group and heating the resulting mixture at a temperature ranging from 50° C. to 150° C. in the absence of a solvent or at a temperature ranging from 30° C. to 150° C. in the presence of an aprotic polar solvent such as dimethylformamide, sulfolane, hexamethylphosphotriamide, etc., to introduce an aromatic nitrogen-containing heterocyclic group to the 7-position wherein the heterocyclic group is connected through the nitrogen atom as described in Japanese Patent Publication No. 36577/82.

(3) Method for Connecting Sulfur Atom:

A coupler having an aromatic mercapto group or a heterocyclic mercapto group at the 7-position thereof can be synthesized using the method as described in U.S. Pat. No. 3,227,554. More specifically, an aryl mercaptan, a heterocyclic mercaptan or a corresponding disulfide is dissolved in a halogenated hydrocarbon type solvent, converted into sulfenyl chloride using chlorine or sulfuryl chloride and added to an aprotic solvent containing a 4-equivalent pyrazolo[1,5-b]-1,2,4-triazole type coupler dissolved therein whereby the desired compound can be synthesized. In order to introduce an alkylmercapto group into the 7-position, a method wherein a mercapto group is introduced into the coupling active position of a coupler and the mercapto group is reacted with a halide to synthesize a 7-alkylthio compound and a method wherein a 7-alkylthio compound is synthesized in one step using an S-(alkylthio)isothiourea hydrochloride (or hydrobromide) as described in U.S. Pat. No. 4,264,723 are useful.

(4) Method for Connecting Carbon Atom:

A coupler releasing a diarylmethane series compound can be synthesized by the method as described in Japanese Patent Publication No. 34937/77, and an aldehydebis type coupler can be synthesized by the methods as described in Japanese Patent Application (OPI) Nos. 105820/76, 129035/78 and 48540/79.

Specific examples of synthesizing the magenta coupler according to the present invention are set forth below.

EXAMPLE 1

Synthesis of 1H-2,6-dimethylpyrazolo[1,5-b]-1,2,4-triazole [Compound (1)]

2,5-Dimethyl-1,3,4-oxadiazole obtained by thermal decomposition of tetraacetyl hydrazine was reacted with benzylamine at 110° C. for 4 hours to synthesize 4-benzyl-3,5-dimethyl-1,2,4-triazole in a yield of 73%.

Melting Point: 125 to 127° C.

75 g of the triazole thus-synthesized was reacted with an aqueous solution of potassium hydroxylamine-O-sulfonate obtained from 66 g of hydroxylamine-O-sulfonic acid and 40 g of potassium hydroxide at 80 to 90° C. for 6 hours. After cooling to room temperature, the pH of the reaction mixture was adjusted to between 8 and 9 using a 50% aqueous solution of potassium carbonate. The potassium sulfate formed was removed by filtration and the filtrate was extracted three times with chloroform. From the chloroform extract 44 g (50% yield) of the triazole which was the starting material was recovered. To the aqueous layer was added a 57% aqueous solution of hydroiodic acid to adjust the pH thereof to 3 under cooling with ice whereby crystals were deposited. The crystals were collected by filtration and recrystallized from ethanol at −20° C. to obtain 39 g (31% yield) of N-aminotriazonium iodide as light yellow crystals.

Melting Point: 180° to 181° C.

Nuclear Magnetic Resonance Spectrum (CDCl$_3$+DMSO-d$_6$): 2.39 (3H, s), 2.67 (3H, brs), 5.35 (2H, s), 6.66 (1H, —N$\underline{H}$), 7.0–7.2 (2H), 7.2–7.46 (4H, —NH included).

8 g of the N-aminotriazonium iodide thus-obtained was dissolved in 50 ml of DMF, to the solution was added 40 ml of acetic anhydride and the mixture was heated to 120° C. Then, 12.5 g of sodium acetate was added and the mixture was stirred at 120° to 130° C. for 4 hours. After removing the DMF and acetic anhydride using an evaporator, the reaction mixture was rendered alkaline with a saturated aqueous sodium carbonate solution and extracted with chloroform. The extract was dried over anhydrous magnesium sulfate and the solvent was removed to obtain a brown oily product. The oily product was purified using a silica gel column with a solvent system of n-hexane and ethyl acetate to obtain 2 g (30% yield) of 7-acetyl-1-benzyl-2,6-dimethylpyrazolo[1,5-b]-1,2,4-triazole.

Melting Point: 105° to 107° C.

Nuclear Magnetic Resonance Spectrum (CDCl$_3$): 2.36 (3H, s), 2.43 (3H, s), 2.60 (3H, s), 5.80 (2H, s), 7.0–7.2 (2H), 7.2–7.36 (3H).

2 g of the 7-acetyl-1-benzyl-2,6-dimethylpyrazolo[1,5-b]-1,2,4-triazole thus-obtained was dissolved in 20 ml of ethanol, to the solution was added 20 ml of concentrated hydrochloric acid and the mixture was refluxed by heating. After about 6 hours, the ethanol was distilled off under reduced pressure, the reaction mixture was rendered alkaline with a saturated aqueous solution of sodium hydrogencarbonate and extracted with ethyl acetate to obtain 1.6 g (95% yield) of almost pure deacetylated compound, i.e., 1-benzyl-2,6-dimethylpyrazolo[1,5-b]-1,2,4-triazole.

Melting Point: 87° to 88° C.

Nuclear Magnetic Resonance Spectrum (CDCl$_3$): 2.32 (3H, s), 2.44 (3H, s), 5.02 (2H, s), 5.22 (1H, s), 7.10–7.40 (5H).

1.6 g of the 1-benzyl-2,6-dimethylpyrazolo[1,5-b]-1,2,4-triazole thus-obtained was reacted with about 0.8 g of metallic sodium in liquid ammonia to obtain 0.67 g (70% yield) of the desired compound i.e., 1H-2,6-dimethylpyrazolo[1,5-b]-1,2,4-triazole as colorless crystals.

Melting Point: 274° to 275° C. (decomposed).

Mass Spectrometry: 136 (M+, 100%).

Elemental Analysis: Calculated (%): C: 52.93; H: 5.92; N: 41.15. Found (%): C: 52.85; H: 6.02; N: 41.01.

Nuclear Magnetic Resonance Spectrum (CDCl$_3$: pyridine-d$_5$=1:1) 2.35 (3H, s), 2.43 (3H, s), 5.50 (1H, s).

EXAMPLE 2

Synthesis of Compound (5)

To a DMF solution of the N-aminotriazonium iodide as described in EXAMPLE 1 was added 1 equivalent of 4-(3-pentadecylphenoxy)butyryl chloride and the mixture was gradually heated from room temperature to 120° C. Then, 6 equivalents of sodium acetate and an excess amount of acetic anhydride were added to the mixture which was heated at between 120° C. and 130° C. for about 6 hours. The same procedure and purification as described in SYNTHESIS EXAMPLE 1 were conducted to obtain 7-acetyl-1-benzyl-2-methyl-6-(3-pentadecylphenoxy)propylpyrazolo[1,5-b]-1,2,4-triazole in a yield of about 30%. Using the compound, 6-(3-pentadecylphenoxy)propylpyrazolo[1,5-b]-1,2,4-triazole was synthesized in the same manner as described in EXAMPLE 1.

EXAMPLE 3

Compound (1) was synthesized using Method II as follows.

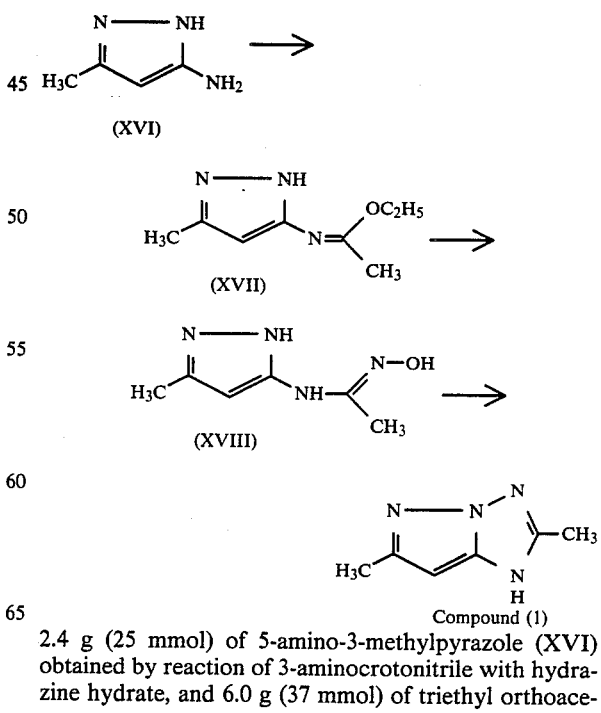

2.4 g (25 mmol) of 5-amino-3-methylpyrazole (XVI) obtained by reaction of 3-aminocrotonitrile with hydrazine hydrate, and 6.0 g (37 mmol) of triethyl orthoacetate were added to 20 ml of toluene and the resulting mixture was refluxed with heating for about 10 hours. The resultant reaction mixture was then distilled to remove the toluene. Consequently, a crude product of (XVII) was obtained in an oily state.

Nuclear Magnetic Resonance Spectrum (CDCl$_3$): 1.28 (3H, 6, J=7.5), 1.96 (3H, s), 2.22 (3H, s), 4.19 (2H, q, J=7.5), and 5.50 (1H, s).

A solution of 2.6 g (37 mmol) of hydroxylamine hydrochloride in 20 ml of methanol was combined with 7.4 ml of a 28% sodium methoxide solution in methanol at 0° C. The resultant mixture was filtered to separate the precipitated sodium chloride. The filtrate was immediately added at 0° C. to a solution of (XVII), obtained as described above, in methanol. At the end of this addition, the resultant mixture was allowed to warm up spontaneously to room temperature, stirred for about 1 hour, and distilled in vacuo to remove the methanol. By washing the resulting crystals with chloroform, 3.2 g (83% in yield) of (XVIII) was obtained.

Melting Point: 180° to 185° C. (decomposition). Nuclear Magnetic Resonance Spectrum (DMSO-d$_6$): 1.87 (3H, s), 2.12 (3H, s), and 5.65 (1H, s).

Elemental Analysis: Calculated (%): C: 46.74; H: 6.54; N: 36.34. Found (%): C: 46.66; H: 6.63; N: 36.10.

In 150 ml of tetrahydrofuran (THF), 1.5 g (9.7 mmol) of (XVIII) produced as described above was dissolved. To the resultant solution, 1.2 g of triethylamine was added and then 2.2 g of p-toluenesulfonyl chloride was added incrementally at room temperature. Then, the resultant mixture was stirred for 30 minutes. The stirred mixture and 150 ml of THF further added thereto were refluxed with heating for 7 hours. The reaction mixture consequently formed was filtered to separate an amine salt formed therein as a precipitate. The filtrate was concentrated. By purifying the concentrate by chromatography, 0.9 g (68% in yield) of compound (1) was obtained. The physical constants determined for Compound (1) were perfectly in agreement with those obtained in EXAMPLE 1. A small amount of Compound (43) was obtained as a secondary product.

Melting Point: 250° to 255° C. (decomposition).

EXAMPLE 4

Compound (44) was synthesized using Method I as follows.

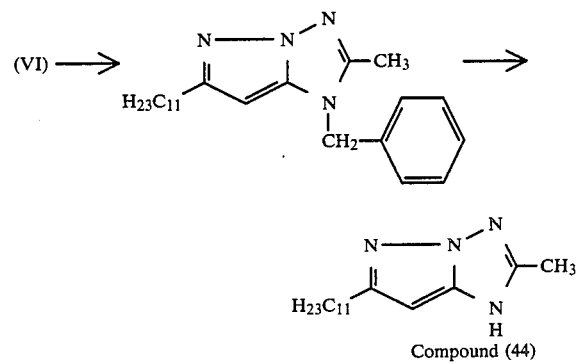

Compound (44)

In 100 ml of DMF, 5 g (16 mmol) of N-aminotriazolium iodide (VI) described in EXAMPLE 1, 5 equivalents, 30 g (79 mmol), of lauric anhydride, and 11 g (77 mmol) of tri-n-propylamine were heated at 140° C. to 150° C. for about 10 hours. The resultant reaction mixture was vacuum-distilled to remove the DMF. The residue after evaporation was combined with ethyl acetate to precipitate unreacted lauric anhydride, which was separated by filtration. The filtrate was transferred into a separatory funnel and thoroughly shaken with a 2 N sodium hydroxide aqueous solution to effect phase separation. The aqueous layer was extracted twice with ethyl acetate. The ethyl acetate layer was washed with a saturated aqueous solution of sodium chloride and then dried over magnesium sulfate. The residue consequently obtained and 30 ml of concentrated hydrochloric acid and 50 ml of ethanol added thereto were refluxed with heating for about 4 hours, then the ethanol removed, and extracted with ethyl acetate. The extract was subjected to conventional work up procedure and purified using a silica gel column. Consequently, 0.8 g (14% in yield) of 1-benzyl derivative was obtained.

Nuclear Magnetic Resonance Spectrum (CDCl$_3$): 0.88 (3H, br t, J=τ7), 1.30 (20H, br s), 2.40 (3H, s), 2.60 (2H, t, J=7.5), 5.03 (2H, s), 5.25 (1H, s), and 7.10–7.45 (5H).

By debenzylation of the 1-benzyl derivative with sodium in liquid ammonia, Compound (44) sparingly soluble in organic solvents except for alcohols was obtained in a yield of about 90%.

Melting Point: 154° to 155° C.

EXAMPLE 5

Compound (6) was synthesized from intermediate (VI) using Method I as follows:

In 8 ml of anhydrous DMF, 1.0 g (3.16 mmol) of (VI) was dissolved. The resultant solution and 3.6 g (15.8 mmol) of benzoic anhydride and 2.3 g (15.8 mmol) of tri-n-propylamine added thereto were stirred at 130° C. for 24 hours. The resultant reaction mixture was distilled under vacuum to remove DMF and tri-n-propylamine. The residue after distillation and 30 ml of ethanol and 10 ml of concentrated hydrochloric acid added thereto were refluxed with heating for 5 days. The resultant reaction mixture was subjected to vacuum distillation to remove the ethanol and concentrated hydrochloric acid. The residue after the distillation was extracted with ethyl acetate. The extract was dried, concentrated, and purified by silica gel chromatography. Consequently, 0.2 g (22% in yield) of the 1-benzyl derivative was obtained.

Nuclear Magnetic Resonance Spectrum (CDCl$_3$): 2.35 (3H, s), 4.95 (2H, s), 5.65 (1H, s), 7.05–7.50 (8H), and 7.80 (2H, dd, J=9.0, 1.5).

By reducing 0.2 g (0.69 mmol) of the 1-benzyl derivative with 0.05 g of sodium in liquid ammonia, 0.12 g (87% in yield) of the desired Compound (6) was obtained.

Melting Point: about 190° C. (gradual decomposition).

EXAMPLE 6

Compound (46) was synthesized by first synthesizing an N-benzyl derivative of Compound (46) from intermediate (VI), using Method I and then removing the protective benzyl group from the N-benzyl derivative.

In 15 ml of N-methyl pyrrolidone, 1.00 g (32 mmol) of (VI) was stirred at room temperature. To the resultant solution, 2.93 g of methoxycarbonyl propionic anhydride and 4.8 ml of tri-n-propylamine were added in the order mentioned. The resultant mixture was heated over an oil bath at 130° C. for 3 hours. The resultant hot mixture was cooled, diluted with ethyl acetate, and washed twice each with 100 ml of cold water. The ethyl acetate layer was dried over anhydrous magnesium sulfate and then concentrated. The concentrate and 30 ml of methanol and 30 ml of concentrated hydrochloric acid added thereto were refluxed with heating for 7 hours. The hot refluxed product was cooled and then subjected to vacuum distillation to remove ethanol. The residue after the vacuum distillation was poured in 100 ml of ice water, neutralized to pH 7, and extracted three times each with 50 ml of ethyl acetate. The ethyl acetate layer was dried over anhydrous magnesium sulfate, concentrated, and purified with a silica gel column (20 g). Consequently, 0.16 g (17% in yield) of an N-benzyl derivative of Compound (46) was obtained in an oily state.

Nuclear Magnetic Resonance Spectrum (CDCl$_3$): 2.42 (3H, s), 2.60–3.15 (4H, m), 3.63 (3H, s), 5.02 (2H, s), 5.26 (1H, s), and 7.12–7.50 (5H, m).

By reducing this N-benzyl derivative with sodium by the procedure described above, Compound (46) was obtained in a yield of about 80%.

Melting Point: 120° to 122° C.

EXAMPLE 7

Compound (48), (49), (9) and (50) were synthesized from intermediate (VI) using Method I as follows:

(VI) $\xrightarrow{\text{7-[4-(p-nitrophenyl)butyryl]-1-benzyl derivative of Compound (47)}}$

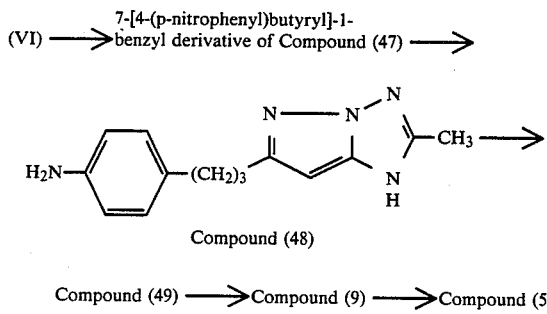

Compound (48)

Compound (49) ⟶ Compound (9) ⟶ Compound (50)

In 150 ml of DMF were dissolved 9.5 g (30 mmol) of (VI), 65 g (150 mmol) of 4-(p-nitrophenyl)butyric anhydride, and 57 ml (300 mmol) of tri-n-propylamine. The resultant mixture was stirred and heated for 4 hours over an oil bath at 130° C., then for 2 hours over an oil bath at 140° C., and further for 6 hours over an oil bath at 160° C. The resultant reaction mixture was subjected to vacuum distillation to remove DMF. The residue after the distillation was dissolved in ethyl acetate. The ethyl acetate solution was washed twice with a 2N NaOH aqueous solution. The ethyl acetate layer was dried over anhydrous magnesium sulfate, then concentrated, and subjected to silica gel column chromatography (using 600 g of silica gel and an eluant formed by mixing hexane with ethyl acetate at 2:1 to 1:1 by volume). Consequently, 7.6 g (45% in yield) of the 7-[4-(p-nitrophenyl)butyryl]-1-benzyl derivative of Compound (47) was obtained.

Nuclear Magnetic Resonance Spectrum (CDCl$_3$): 2.40 (3H, s), 1.8–3.3 (12H, m), ~5.80 (2H, s), 7.0–7.4 (9H, m), and 8.1 (4H, m).

In a mixed solvent of 150 ml of EtOH and 50 ml of concentrated hydrochloric acid, 7.6 g (13 mmol) of the 7-[4-(p-nitrophenyl)butyryl]-1-benzyl derivative of Compound (47) was refluxed with heating for 10 hours. The resultant reaction mixture was combined with 100 ml of water and subjected to vacuum concentration to remove the ethanol. The residue after the vacuum concentration was neutralized with aqueous ammonia and extracted with ethyl acetate. The ethyl acetate layer was dried over anhydrous magnesium sulfate, concentrated, and subjected to silica gel column chromatography (using 140 g of silica gel and an eluant formed by mixing hexane with ethyl acetate at a ratio of 1:1 by volume). Consequently, 3.8 g (76% in yield) of the N-benzyl derivative of Compound (47) was obtained.

Nuclear Magnetic Resonance Spectrum (CDCl$_3$): 2.03 (2H, m), 2.44 (3H, s), 2.58–2.85 (4H, m) 5.02 (2H, s), 5.20 (1H, s), 7.04–7.40 (7H, m) and 8.04 (2H, d, J=8.0).

In 80 ml of isopropyl alcohol, 18 g (0.32 mmol) of reduced iron, 1.3 g (25 mmol) of ammonium chloride, and 8 ml of cold water were vigorously stirred and heated until refluxing was achieved The resultant reaction mixture and 0.2 ml of concentrated hydrochloric acid added thereto were refluxed with heating for 30 minutes. To the refluxed mixture, 18.0 g (47.9 mmol) of the aforementioned 6-[3-(p-nitrophenyl)propyl]-1-benzyl derivative of Compound (47) was added incrementally over a period of 20 minutes. The resultant mixture was refluxed with heating for 1 hour. The reaction mixture was filtered through celite. The celite was thoroughly washed with ethanol. The filtrate was concentrated, dissolved in ethyl acetate, washed with cold water, and then dried over anhydrous magnesium sulfate. By concentrating the resultant product, 15.8 g (95% in yield) of the 1-benzyl derivative of Compound (48) was obtained. Nuclear Magnetic Resonance Spectrum (CDCl$_3$): 1.95 (2H, m), 2.38 (3H, s), 2.40–2.76 (4H, m), 3.36 (2H, br), 4.97 (2H, s), 5.20 (1H, s), 6.53 (2H, m), 5.91 (2H, m), and 7.00–7.38 (5H, m).

The 1-benzyl derivative of Compound (48) in the amount of 15.8 g (45.7 mmol) was added to 200 ml of liquid ammonia in a refluxing state and the resulting mixture was stirred. To the resultant mixture, 2.6 g (0.11 mol) of metallic solium was added incrementally. Then ammonium chloride was added thereto incrementally. The resulting mixture was allowed to stand overnight to remove ammonia. The residue was dissolved in a 2N HCl aqueous solution and washed with ethyl acetate. The aqueous layer was neutralized with aqueous ammonia and then filtered to separate the precipitate consequently formed therein. The precipitate was washed first with cold water and then with acetonitrile and thereafter dried. Consequently, 7.9 g (68% in yield) of Compound (48) was obtained in a substantially pure state.

Nuclear Magnetic Resonance Spectrum (CDCl$_3$+DMSO-d$_6$): 1.88 (2H, br, quintet, J=~7), 2.41 (3H, s), 2.3–2.8 (4H), 5.42 (1H, s), 6.56 (2H, d, J=8.5), and 6.90 (2H, d, J=8.5).

Compound (48) in the amount of 3.00 g (11.7 mmol) was mixed first with 50 ml of acetonitrile and then with 25 ml of N,N-dimethylacetamide and the resultant mixture was stirred and heated until refluxing was achieved. To the mixture, a solution of 7.19 g (12.9 mmol) of the acid chloride

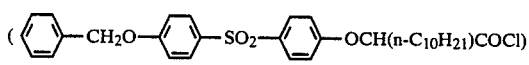

in 20 ml of acetonitrile was added dropwise over a 20 minute period. The resultant mixture was further refluxed for 20 minutes. Then, with a solution of 0.72 g (0.13 mmol) of the same acid chloride in 10 ml of acetamide added dropwise thereto over a 10 minute period, the reaction mixture was further refluxed for 30 minutes. The hot mixture resulting from the refluxing was cooled, poured in 500 ml of cold water, and extracted with ethyl acetate. The ethyl acetate layer was dried over anhydrous magnesium sulfate, concentrated, and subjected to silica gel column chromatography (using 300 g of silica gel and an eluate obtained by mixing chloroform with methanol at a ratio of 60:1 by volume). Consequently, 7.25 g (80% in yield) of Compound (49) was obtained in a solid state.

Elemental Analysis: Calculated (%): C: 69.65; H: 6.88; N: 9.02; S: 4.13. Found (%): C: 68.99; H: 6.90; N: 8.90; S: 4.07.

Mass Analysis (FD): 776 ($M^+$, b.p.).

Nuclear Magnetic Resonance Spectrum (CDCl$_3$): 0.86 (3H, br t, J=7), 1.0–2.2 (20H, m), 2.38 (3H, s), 2.5–2.8 (4H, m), 4.68 (1H, br t, J=6), 5.05 (2H, s), 5.45 (1H, s), 6.9–7.4 (13H, m), 7.7–7.9 (4H, m), 8.17 (1H, s), and 11.6 (1H, br).

A solution of 3.3 g (4.3 mmol) of the 6-[3-(p-nitrophenyl)propyl]-1-benzyl derivative of Compound (47) in 60 ml of THF was combined with 0.66 g of 10% Pd/C. The resultant mixture was stirred at 60° C. under a hydrogen pressure of 60 atmospheres for 3 hours. The stirred mixture was cooled and filtered to separate the catalyst. The filtrate was concentrated. By subjecting the concentrated filtrate to silica gel column chromatography (using 90 g of silica gel and an eluent obtained by mixing chloroform with methanol at a ratio of 1:0 to 30:1 by volume), 2.7 g (92% in yield) of Compound (9) in a solid state was obtained.

Mass Analysis (FD): 687 ($M^+ +2$, 50%), 686 ($M^+ +1$, 100) 685 ($M^+$, 30).

In 100 ml of dichloromethane, 4.25 g (6.20 mmol) of Compound (9) and 50 ml of THF were stirred at room temperature to effect solution. The resultant solution and 795 mg (5.95 mmol) of N-chloro-succinimide added thereto were stirred at room temperature for 15 minutes. The resultant mixture was washed twice each with 150 ml of cold water, and then dried over anhydrous magnesium sulfate. The resultant mixture was concentrated and then subjected to silica gel column chromatography (using 700 g of silica gel and an eluant formed by mixing chloroform with methanol in a ratio of 50:1 to 30:1 by volume). Consequently, 4.04 g (90% in yield) of Compound (50) in a solid state was obtained. Mass Analysis (FD): 722, 721, and 720 (9:7:9), 220 (b.p.)

EXAMPLE 8

Compound (17) was synthesized through the Compound (51) from Compound (48) as the starting material.

In 30 ml of acetonitrile, 1.79 g (7.00 mmol) of Compound (48) and 5 ml of N,N-dimethylacetamide were stirred under application of heat until the resultant mixture was refluxed. To the resultant mixture, a solution of 2.83 g (7.70 mmol) of the acid chloride, [(t—C$_5$H$_{11}$)$_2$C$_6$H$_3$OCH(n—C$_4$H$_9$)COCl], in 10 ml of acetonitrile was added dropwise over a 15 minute period. The resultant mixture was further refluxed for 30 minutes. The resultant hot mixture was cooled, poured into 300 ml of cold water, and extracted using ethyl acetate. The ethyl acetate layer was dried over anhydrous magnesium sulfate, then concentrated, and subjected to silica gel column chromatography (using 100 g of silica gel and an eluant obtained by mixing chloroform with methanol in a ratio of 70:1 by volume). Consequently, 3.12 g (76% in yield) of Compound (51) in a solid state was obtained.

Elemental Analysis: Calculated (%): C: 73.81; H: 8.77; N: 11.95. Found (%): C: 73.64; H: 8.95; N: 11.93.

Nuclear Magnetic Resonance Spectrum (CDCl$_3$): 0.50–1.00 (7H, m), 1.00–2.16 (26H, m), 2.44 (3H, s), 2.46–2.80 (4H, m), 4.66 (1H, t, J=6.0), 5.44 (1H, s), 6.90–7.34 (6H, m), and 7.64 (1H, d, J=9.0).

In 100 ml of dichloromethane, 3.10 g (5.29 mmol) of Compound (51) and 50 ml of THF were stirred at room temperature to effect solution. The resultant solution and 706 mg (5.29 mmol) of N-chloro-succinimide added thereto were stirred for 10 minutes. The resultant mixture was washed twice each with 150 ml of cold water, and then dried over anhydrous magnesium sulfate. The reaction mixture was concentrated, crystallized by addition of acetonitrile, and refluxed with heating once. The resulting reaction mixture was cooled, separated off by filtration, washed with acetonitrile, and then dried. Consequently, 2.4 g (73% in yield) of Compound (17) in a solid state was obtained.

Elemental Analysis: Calculated (%): C: 69.71; H: 8.12; N: 11.29; Cl: 5.72. Found (%): C: 69.36; H: 8.21; N: 11.25; Cl: 5.78.

Nuclear Magnetic Resonance Spectrum (CDCl$_3$): 0.48–1.00 (7H, m), 1.06–2.18 (26H, m), 2.45 (3H, s), 2.48–2.82 (4H, m), 4.67 (1H, t, J=6.0), 6.65 (1H, d, J=8.5), 6.91–7.34 (6H, m), and 7.87 (1H, s).

EXAMPLE 9

A fluorine-containing aliphatic carboxylic acid amide group was introduced as a coupling-off group in the 7-position of Compound (51).

In 25 ml of acetic acid, 2.93 g (5.00 mmol) of Compound (51) was stirred at room temperature. Into the resultant solution, 586 mg (5.00 mmol) of isoamyl nitrite was added dropwise. Then, the resultant mixture was stirred for one hour. The resultant mixture was gradually added to 300 ml of water. The reaction mixture was filtered to separate the precipitate. The separated precipitate was washed with cold water and dried under a vacuum. Consequently, 2.95 g (96% in yield) of a 7-nitroso derivative in a solid state was obtained.

In 50 ml of ethanol, 2.85 g (4.63 mmol) of the 7-nitroso derivative was heated under an atmosphere of nitrogen until the resultant mixture was refluxed. Into the resultant mixture, a solution of 4.38 g (23.1 mmol) of stannous chloride in 10 ml of concentrated hydrochloric acid was added dropwise over a period of 10 minutes. The resultant mixture was refluxed for 30 minutes and then cooled. The reaction mixture thus obtained was poured into 150 ml of cold water and extracted using ethyl acetate. The ethyl acetate layer was dried over anhydrous magnesium sulfate and then concentrated to dryness. The resultant dry mass was dissolved in 25 ml of pyridine and then cooled and stirred under a nitrogen atmosphere. To the stirred solution, 2.15 g (4.63 mmol) of the acid chloride, [H(CF$_2$)$_8$COCl], was added dropwise, with the stirring being continued for 1 hour. The resultant reaction mixture was poured into 250 ml of cold water and then extracted with ethyl acetate. The ethyl acetate layer was washed with 2N hydrochloric acid and then washed with cold water. The ethyl acetate layer was dried over anhydrous magnesium sulfate, then concentrated, and subjected to silica gel column chromatography (using 150 g of silica gel and an eluant obtained by mixing chlorgform with methanol in a ratio of 100:1). By concentrating and drying the eluate, 3.43 g (72% in yield) of Compound (52) was obtained.

Nuclear Magnetic Resonance Spectrum (CDCl$_3$): 0.52–1.01 (7H, m), 1.02–2.15 (26H, m), 2.42 (3H, s), 2.46–2.78 (4H, m), 4.60 (1H, t, J=6.0), 6.30 (1H, tt, J=51.0, 5.0), 4.5 (1H, d, J=8.5), 6.85–7.36 (6H, m), 8.90 (1H, brs), 10.0 (1H, brs), and 10.3 (1H, brs).

EXAMPLE 10

Compound (59) was synthesized using Method II as follows. The final product was obtained from 5-amino-3-methyl pyrazole corresponding to (XII-A).

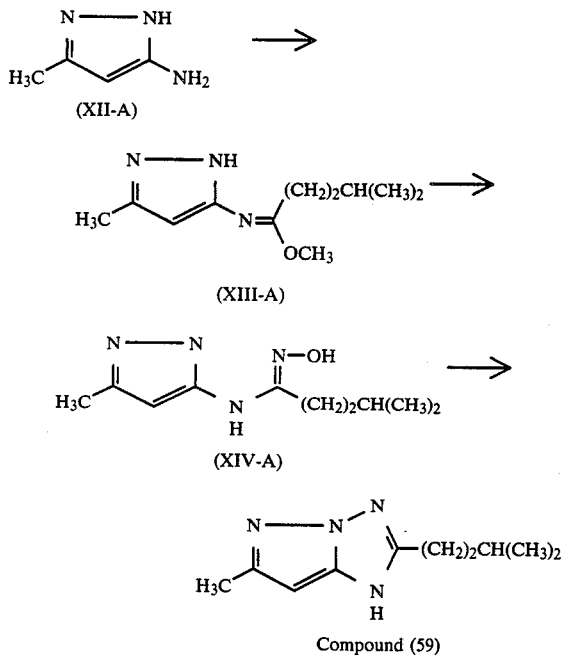

Compound (59)

Trimethyl orthoisocaproate could be synthesized in a yield of about 50% from isocapronitrile via the imidate hydrochloride. Boiling point 75° to 77° C./28 mmHg.

In 200 ml of toluene, 19.8 g (0.11 mol) of the ortho ester and 10.9 g (0.11 mol) of (XII-A) were refluxed with heating for about 24 hours and thereafter subjected to vacuum distillation to remove the toluene. Consequently, a crude product of (XIII-A) in an oily state was obtained.

To this crude product was added at 0° C. a methanol solution of hydroxylamine prepared from 11.7 g (0.17 mol) of hydroxylamine hydrochloride and 34 ml of 28% sodium methoxide and then stirred at room temperature for 1 hour. The resultant reaction mixture was subjected to vacuum distillation to remove the methanol. The residue was combined with chloroform to precipitate fine crystals of (XIV-A). By filtering this mixture, 12 g (52% in yield) of crystals was obtained. The crystals were dissolved in 3 liters of tetrahydrofuran. The resultant solution and 6.9 g (68 mmol) of triethylamine and 13.1 g (68 mmol) of p-toluenesulfonyl chloride added thereto were treated by following the procedure as described in EXAMPLE 3. Consequently, 7.1 g (65% in yield) of compound (59) was obtained.

Melting Point: 140 to 142° C.

Mass Analysis: 192 (M+), 136 (b.p.).

Nuclear Magnetic Resonance Spectrum (CDCl$_3$): 0.90 (6H, d, J=6), 1.55–1.90 (3H), 2.45 (3H, s), 2.90 (2H, brt, J=7), 5.60 (1H, s), 13.3 (1H).

EXAMPLE 11

Compound (54) was synthesized using Method III as follows.

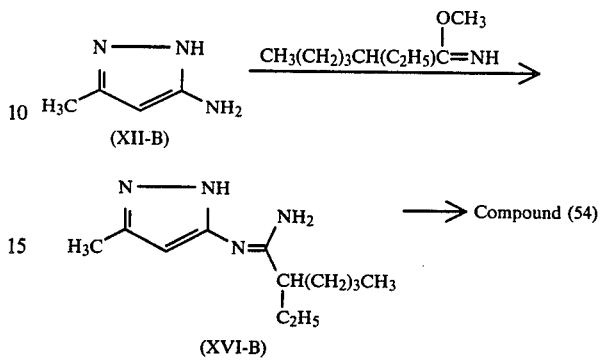

From 2-ethylhexanoyl chloride, 2-ethylhexanonitrile was synthesized by the method described in Org. Syn. Coll., Vol. 3, p. 490 (1955). This product was dissolved in 1 equivalent of methanol. The resultant solution was allowed to absorb 1 equivalent of dry hydrogen chloride gas at 0° C. When the absorbate was allowed to stand in a refrigerator at −5° C. for about 20 days, crystals of the methylimidate hydrochloride were precipitated. The mixture was combined with diethyl ether and then filtered to separate the crystals in a yield of 48%.

In 150 ml of methanol, 10 g (51.6 mmol) of the imidate hydrochloride and 5 g (51.5 mmol) of (XII-B) were stirred at 40° C. After about 7 hours of stirring, two spots were observed in TLC (using silica gel and an eluant obtained by mixing chloroform with ethanol in a ratio of 4:1 by vol.). The spot of lower polarity had the structure of (XIII). The solution and an excess amount of ammonium chloride added thereto were refluxed with heating for about 2 hours. Consequently, (XIII) vanished and (XVI) alone remained. The resultant reaction mixture was subjected to vacuum distillation to remove the methanol. The residue was combined with 50 ml of chloroform and 10 ml of methanol and the resultant mixture was filtered to remove insolubles. The filtrate was concentrated and purified with a small amount of silica gel in a column. Consequently, 8 g (70% in yield) of (XVI) in an oily state was obtained.

Nuclear Magnetic Resonance Spectrum (CDCl$_3$:CD$_3$OD=3:2). 0.7–1.2 (6H), 1.2–1.6 (4H), 1.6–2.1 (4H), 2.32 (3H, s), 2.80 (1H, quintet J=7), 5.70 (3H, broad), and 6.20 (1H, s).

In 50 ml of acetic acid, 2.6 g (12 mmol) of (XVI) was dissolved. At room temperature, 5.8 g (12 mmol) of lead tetraacetate was added incrementally to the resultant solution under a nitrogen atmosphere. After the addition, the resultant mixture was refluxed with heating for 3 hours. The resultant reaction mixture was subjected to vacuum distillation to remove the acetic acid, extracted three times, each time with a 30:1 by volume mixed solvent of chloroform and ethanol, washed with a saturated aqueous sodium bicarbonate solution and an aqueous sodium chloride solution, and dried with magnesium sulfate. The resultant reaction mixture was filtered, concentrated, and purified by silica gel column chromatography. Consequently, 0.15 g (5.7% in yield) of Compound (54) was obtained.

Melting Point: 110° to 115° C.

Mass Analysis: 220 (M+), 155, 130.

Nuclear magnetic Resonance Spectrum (CDCl$_3$): 0.7–1.2 (6H), 1.2–1.55 (4H), 1.55–2.20 (4H), 2.45 (3H, s), 2.95 (1H, quintet, J=7), 5.62 (1H, s), and 12.6 (1H).

EXAMPLE 12

Compound (55) was synthesized by Method II as follows.

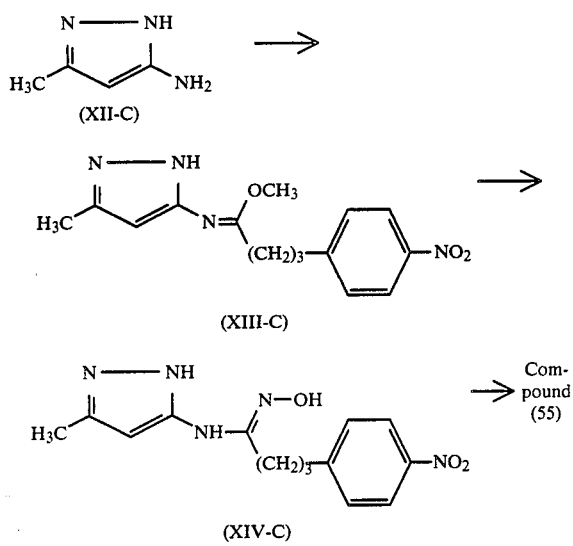

In 100 ml of toluene, 9.2 g (34 mmol) of trimethyl orhto-4-(p-nitrophenyl)butyrate and 5 g (51 mmol) of 3-amino-5-methyl pyrazole (XII-C) were refluxed with heating for 10 hours. The resultant mixture was subjected to vacuum distillation to remove the toluene. The (XIII-C) thus obtained in a crude form was dissolved in 100 ml of methanol. To the resultant solution, a methanol solution of hydroxylamine prepared from 3.5 g (50 mmol) of hydroxylamine hydrochloride as described in EXAMPLE 3 was added at 0° C. After this addition, the resultant mixture was stirred at room temperature for 1 hour. The stirred mixed solution was subjected to vacuum distillation to remove the solvent. When the residue after the distillation and 30 ml of dichloromethane added thereto were allowed to stand, crystals of (XIV-C) precipitated in the solution. Yield 6.7 g (65%), melting point 190° to 193° C. (decomposition).

In 500 ml of tetrahydrofuran (THF), 2 g (6.6 mmol) of (XIV-C) was dissolved. The resultant solution and 0.73 g (7.3 mmol) of triethylamine added thereto were stirred. Into the stirred mixture, a solution of 1.4 g (7.3 mmol) of p-toluenesulfonyl chloride in 50 ml of THF was gradually added. After this addition, the stirring of the mixture was continued for about 1 hour to induce precipitation of triethylamine hydrochloride salt. This mixture was filtered to separate the precipitate. The separated precipitate was washed with 150 ml of THF. The filtrate was refluxed with heating under a nitrogen atmosphere for about 7 hours and, thereafter, distilled under a vacuum to remove the THF. The residue was purified by silica gel chromatography. Consequently, 1.2 g (63% in yield) of Compound (55) was obtained.

Melting Point: ~152° C.

Mass Analysis: 285 (M+), 149 (b.p.).

Nuclear Magnetic Resonance Spectrum (DMSO-d$_6$): 2.05 (2H, m), 2.45 (3H, s), 2.56–2.86 (4H, m), 5.60 (1H, s), 7.25 (2H, d, J=8.0), and 8.05 (2H, d, J=8.0)

EXAMPLE 13

Compound (62) was sythesized starting with Compound (55) via Compounds (56) and (58).

In 100 ml of isopropyl alcohol, 20 g (0.36 mol) of reduced iron, 1.4 g (28 mmol) of ammonium chloride, and 10 ml of water were vigorously stirred and heated until the resultant mixture was refluxed. The resultant mixture and 0.3 ml of concentrated hydrochloric acid added thereto were refluxed with heating for 30 minutes. To the resluxed mixture, 15.2 g (53.2 mmol) of Compound (55) was added incrementally over a period of 20 minutes. The resultant mixture was refluxed with heating for one hour. The refluxed mixture was filtered through celite and thoroughly washed with ethanol. The filtrate was concentrated, dissolved in a 2N HCl aqueous solution, and washed with ethyl acetate. The aqueous layer was neutralized with aqueous ammonia to induce precipitation and filtered to separate the precipitate. The separated precipitate was washed first with cold water and then with acetonitrile and, thereafter, dried. Consequently, 10.9 g (80% in yield) of Compound (56) in a substantially pure state was obtained.

Melting Point: ~180° C.

Nuclear Magnetic Resonance Spectrum (DMSO-d$_6$): 1.90 (2H, br, quintet, J=~7), 2.46 (3H, s), 2.3–2.8 (4H), 5.60 (1H, s), 6.55 (2H, d, J=8.5), and 6.93 (2H, d, J=8.5).

Compound (56) in the amount of 3.6 g (14.0 mol) and a mixed solvent of 30 ml of N,N-dimethylacetamide and 60 ml of acetonitrile added thereto were refluxed with heating. Into the resultant mixture, a solution-of 6.1 g (15.4 mmol) of the acid chloride, [(t-C$_5$H$_{11}$)2-C$_6$H$_3$OCH(n-C$_6$H$_{13}$)COCl], in 20 ml of acetonitrile was added dropwise over a period of 20 minutes. The resultant mixture was refluxed with heating for 30 minutes. The hot mixture was cooled, poured into 300 ml of cold water, and extracted using ethyl acetate. The extract was washed with a saturated sodium chloride aqueous solution, dried over anhydrous magnesium sulfate, concentrated, and subjected to silica gel column chromatography. Consequently, 7.0 g (81% in yield) of Compound (58) was obtained.

Nuclear Magnetic Resonance Spectrum (CDCl$_3$): 0.50–1.00 (7H, m), 1.00–2.15 (30H, m), 2.45 (3H, s), 2.46–2.80 (4H, m), 4.68 (1H, t, J=6.5), 5.60 (1H, s), 6.88–7.33 (6H, m), 7.66 (1H, d, J=9.0), and 7.88 (1H, br, s).

Compound (58)in the amount of 3.1 g (5.00 mmol) and 25 ml of acetic acid added thereto were stirred at room temperature. Into the resultant solution, 586 mg (5.00 mmol) of isoamyl nitrite was added dropwise. The resultant mixture was stirred for one hour. The stirred mixture was gradually added to 300 ml of cold water to induce precipitation. The precipitate was separated by filtering the mixture and then washed with cold water. The precipitate was dried under a vacuum. Consequently, 2.9 g (91% in yield) of the 7-nitroso derivative in a solid state was obtained.

The 7-nitroso derivative in the amount of 2.9 g (4.5 mmol) was dissolved in 50 ml of ethanol. The solution was heated under a nitrogen atmosphere until it refluxed. To the refluxed solution, a solution of 4.27 g (22.5 mmol) of stannous chloride in 10 ml of concentrated hydrochloric acid was added dropwise over a period of 10 minutes. The resultant mixture was refluxed with heating for 30 minutes, then cooled, poured into 150 ml of cold water, and extracted using ethyl acetate. The ethyl acetate layer was dried over anhydrous magnesium sulfate and then concentrated to dryness. The dry mass thus obtained and 100 ml of toluene and 0.49 g (5.0 mmol) of 2,5-dimethyl-1,3,4-oxadiazole added thereto were refluxed with heating for about 5 hours. The refluxed mixture was poured into 250 ml of cold water and extracted using ethyl acetate. The ethyl acetate layer was dried over anhydrous magnesium sulfate, concentrated, and subjected to silica gel column chromatography. Consequently, 2.2 g (70% in yield) of Compound (62) in a solid state was obtained.

Melting Point: ~120° C.

Nuclear Magnetic Resonance Spectrum (CDCl$_3$): 0.48–1.00 (7H, m), 1.05–2.20 (30H, m), 2.43 (3H, s), 2.46 (6H, s , 2,46–2.80 (4H, m), 4.67 (1H, t, J=6.5), 6.60 (1H, d, J=8.5), 6.90–7.35 (6H, m), and 7.85 (1H, s).

REFERENCE EXAMPLE 1

1.1 millimol of each of Compound (1) according to the present invention and Comparison Compound A represented by the chemical structural formula shown below was dissolved in 10 ml of ethanol. In the solution, 1.3 millimole of 4-N-ethyl-N-(2-methanesulfonamidoethyl)amino-2-methylaniline monosulfate, which is a color developing agent, was suspended. Then, an aqueous solution containing 12.9 millimole of anhydrous sodium carbonate dissolved in 5 ml of water was added thereto and the mixture was stirred at room temperature. To the mixture solution, 10 ml of an aqueous solution containing 2.4 millimole of potassium persulfate dissolved was gradually added dropwise.

After thoroughly stirring for 1 hour at room temperature, the reaction mixture was subjected to an extraction treatment by adding 50 ml of ethyl acetate and 30 ml of water. The ethyl acetate layer was washed thoroughly with a saturated sodium chloride aqueous solution and then the solvent was removed therefrom. The residue was separated using silica gel column chromatography. The eluate used was ethyl ether. The NMR spectrum of the magenta dye formed from Compound (1) according to the present invention measured in heavy chloroform (CDCl$_3$) was as follows:

1.24 (3H, t, J=7.2), 2.45 (3H, s), 2.52 (6H, s), 2.98 (3H, s), 3.24–3.78 (6H), 4.64 (1H, brt, J=7), 6.60–6.80 (2H), 8.84 (1H, d, J=9.0).

The absorptions underlined correspond to four methyl groups and thus the structure of the magenta dye is confirmed to be the formula shown below. The melting point of the magenta dye is 244° to 245° C.

Comparison Compound A

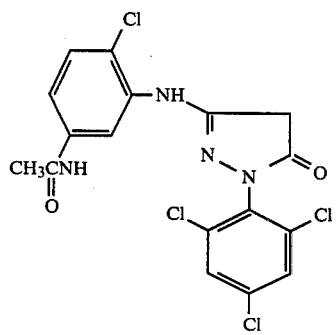

Magenta Dye B

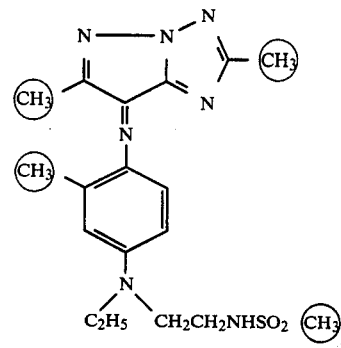

(wherein the methyl groups in the circles correspond to the methyl groups exhibiting the above-described chemical shifts in the NMR spectrum).

Visible absorption spectra of Magenta Dye B and the magenta dye formed from Comparison Compound A in ethyl acetate are shown in FIG. 1. In FIG. 1 the absorption spectral curves are normalized taking the maximum density as 1.0 for comparison.

It is apparent from FIG. 1 that the dye obtained from the coupler according to the present invention has the $\lambda_{max}$ coincident with that of the dye formed from Comparison Compound (A), no subsidiary absorptions in the range from 400 nm to 430 nm and sharply cut absorption curve at the longer wavelength side. Therefore, the coupler according to the present invention is advantageous in color reproduction when it is employed in a color photographic light-sensitive material.

REFERENCE EXAMPLE 2

13 g of Comparison Compound C shown below was dissolved together with 15 ml of trioctyl phosphate and 15 ml of ethyl acetate. The resulting solution was added to 100 g of a 10% aqueous gelatin solution containing sodium di-sec-butylnaphthalenesulfonate, and the mixture was stirred and dispersed by means of a homogenizer to prepare a dispersion. The dispersion thus-prepared was mixed with 300 g of a green-sensitive silver chlorobromide emulsion (containing 13.5 g of silver, and having a bromide content of 45 mol % and a chloride content of 55 mol %) and thereto were added sodium dodecylbenzenesulfonate as a coating aid and 2-hydroxy-4,6-dichloro-s-triazine as a hardener. The mixture was coated on a cellulose triacetate support to form an emulsion layer. Further, a gelatin coating solution was applied to the emulsion layer as a protective layer at a coverage of 1 g gelatin per square meter, and dried. The light-sensitive material thus-prepared was designated Film A.

Comparison Compound C

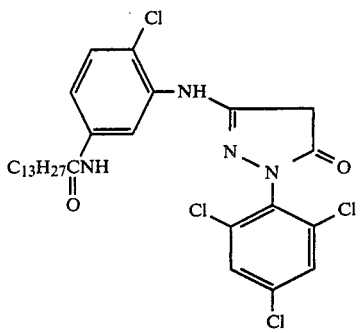

Also, Film B was prepared in the same manner as described for Film A except using 9.9 g of Compound (5) according to the present invention in place of Comparison Compound C.

Further, Film C was prepared in the same manner as described for Film A except that 10.6 g of Compound (13) according to the present invention was used in place of Comparison Compound C and the amount of the green-sensitive silver chlorobromide emulsion was reduced to 200 g.

Films A to C described above were exposed to light using a sensitometer under the condition of 1,000 lux.1 sec. and subjected to the following development processing.

| Processing Step | Temperature (°C.) | Time |
| --- | --- | --- |
| Development | 33 | 3 min 30 sec |
| Bleach-Fixing | 33 | 1 min 30 sec |
| Washing | 28-35 | 3 min |

The processing solutions used have the following compositions.

| Developing Solution | |
| --- | --- |
| Benzyl Alcohol | 15 ml |
| Diethylenetriaminepentaacetic Acid | 5 g |
| Potassium Bromide | 0.4 g |
| Sodium Sulfite | 5 g |
| Sodium Carbonate | 30 g |
| Hydroxylamine Sulfate | 2 g |
| 4-Amino-3-methyl-N—ethyl-N—β-(methane sulfonamido)ethylaniline Sesquisulfate Monohydrate | 4.5 g |
| Water to make | 1,000 ml (pH = 10.1) |

| Bleach-Fixing Solution | |
| --- | --- |
| Ammonium Thiosulfate (70 wt %) | 150 ml |
| Sodium Sulfite | 5 g |
| Sodium Ethylenediaminetetraacetato Iron (III) | 40 g |
| Ethylenediaminetetraacetic Acid | 4 g |
| Water to make | 1,000 ml (pH = 6.8) |

The densities of dye images after the color development processing were measured using a Macbeth densitometer with a Status AA filter. Further, the absorption spectra of the dye images were measured. It was found that the absorption of each dye image of the present invention on the film had no subsidiary absorption and the absorption curve on the longer wavelength side was cut sharply similar to the results of Example 1. The color forming characteristics are shown in the following Table.

TABLE

| Film | Compound | Mole Ratio of Ag/Cp | Maximum Density | Maximum Absorption Wavelength (nm) | Subsidiary Absorption (density at 420 nm)* |
| --- | --- | --- | --- | --- | --- |
| A | Comparison Compound C | 6 | 2.62 | 535 | 0.137 |
| B | Compound (5) (Present Invention) | 6 | 2.60 | 536 | 0.049 |
| C | Compound (13) (Present Invention) | 4 | 3.20 | 536 | 0.048 |

*The density was obtained by taking the maximum density as 1.0.

The results in the Table above show that the couplers according to the present invention provide sufficiently high color densities compared with a conventional 5-pyrazolone type coupler. In particular, a 2-equivalent coupler represented by Compound (13) provides a high color density in spite of a small amount of silver coated.

In addition, the subsidiary absorptions in the range around 420 nm were extremely low with respect to the couplers according to the present invention in comparison with that of the comparison coupler. Therefore, excellent color reproduction can be achieved by the couplers according to the present invention.

While the invention has been described in detail and with reference to specific embodiments thereof, it will be apparent to one skilled in the art that various changes and modifications can be made therein without departing from the spirit and scope thereof.

What is claimed is:

1. A novel pyrazolo[1,5-b]-1,2,4-triazole derivative compound represented by general formula (I):

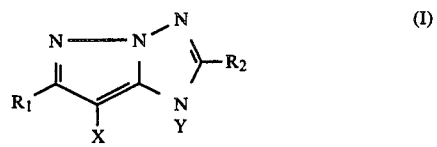

wherein $R_1$ and $R_2$ are independently a hydrogen atom or a substituent; X is a hydrogen atom or a group capable of being released upon coupling; Y represents a hydrogen atom or an aralkyl group.

2. A compound as claimed in claim 1, wherein $R_1$ and $R_2$ are independently a hydrogen atom, a halogen atom, an aliphatic residue, an aryl group, a heterocyclic group, a cyano group, an alkoxy group, an aryloxy group, an acylamino group, an anilino group, a ureido group, a sulfamoylamino group, an alkylthio group, an arylthio group, an alkoxycarbonylamino group, a sulfonamido group, a carbamoyl group, a sulfamoyl group, a sulfonyl group, a heterocyclicoxy group, an acyloxy group, a carbamoyloxy group, a silyloxy group, an aryloxycarbonylamino group, an imido group, a heterocyclicthio group, a sulfinyl group, a phosphonyl group, an aryloxycarbonyl group, an acyl group or an alkoxycarbonyl group.

3. A compound as claimed in claim 1, wherein X is a hydrogen atom, a halogen atom, a carboxy group or a -continued
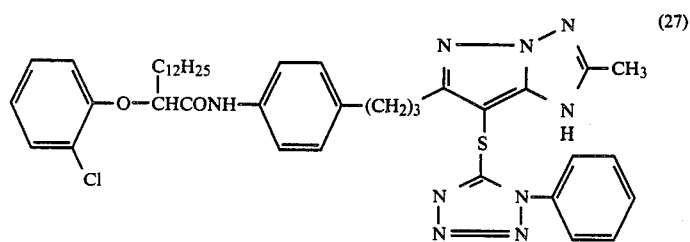
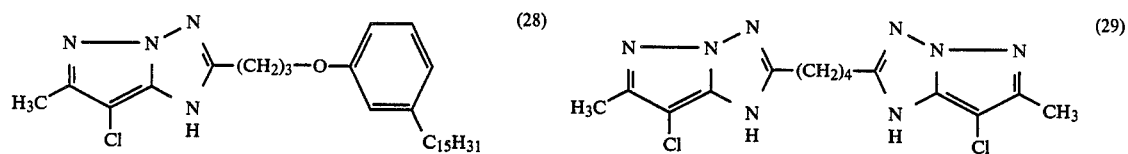
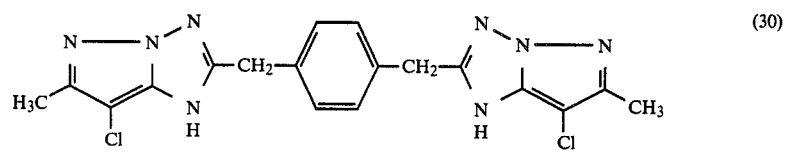
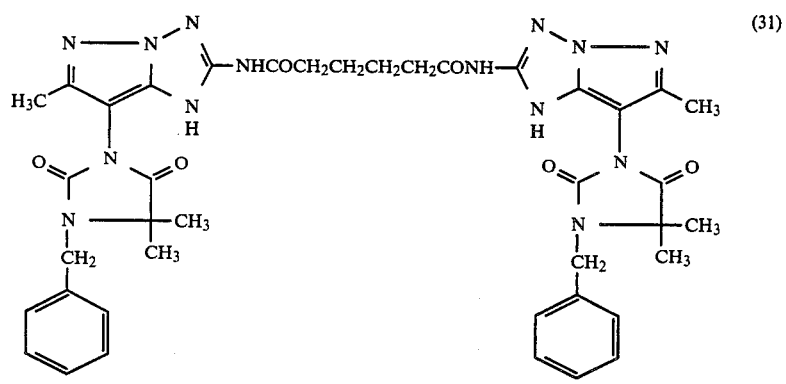
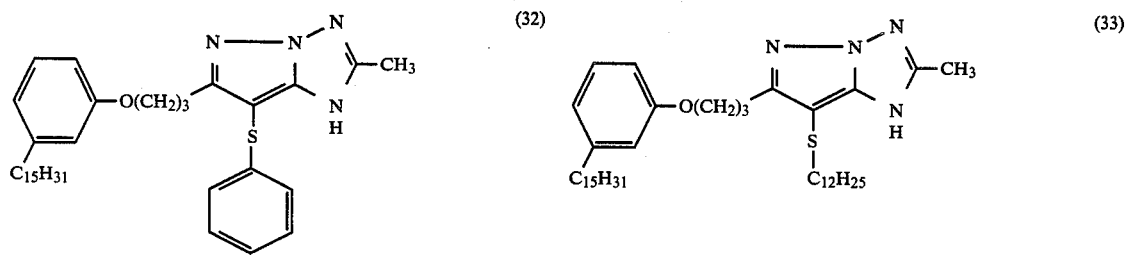
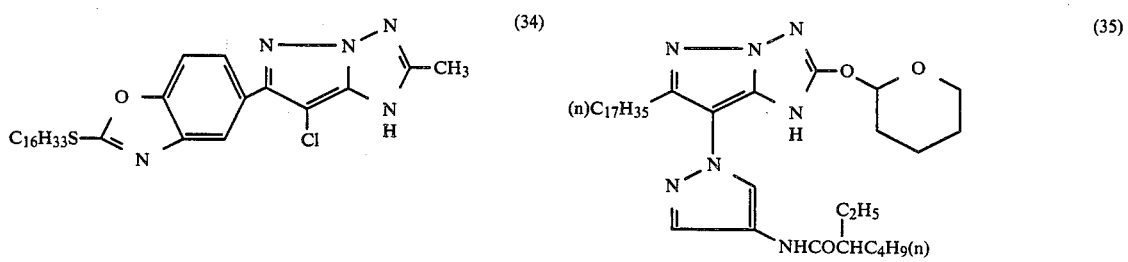

-continued
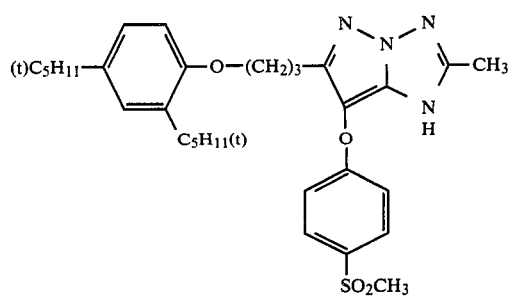 (18)
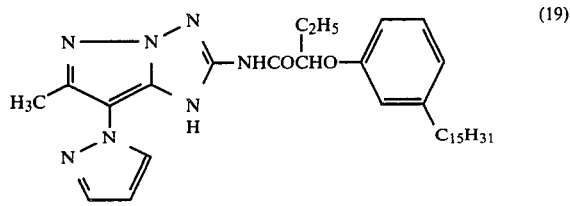 (19)
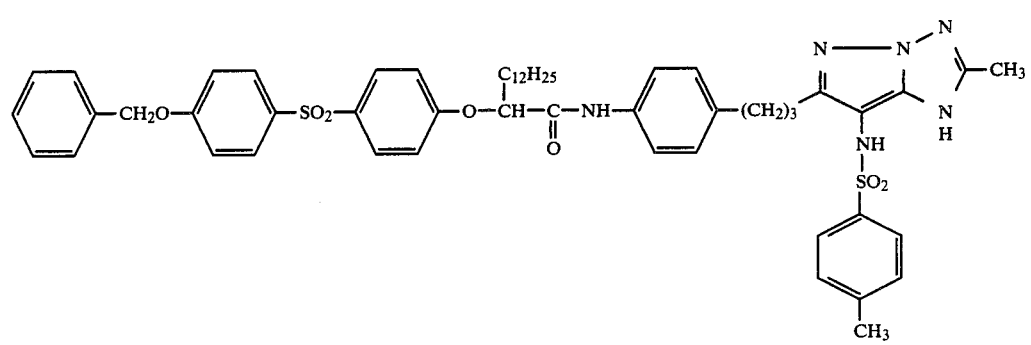 (20)
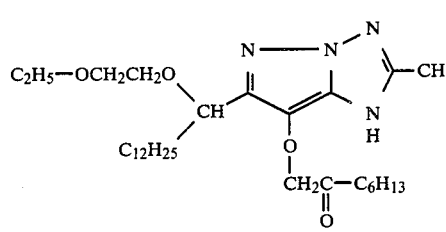 (21)
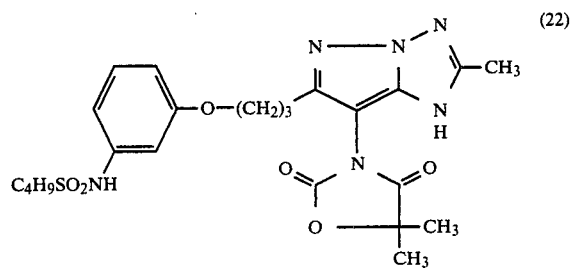 (22)
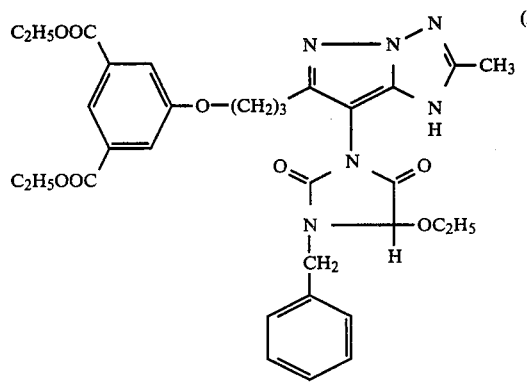 (23)
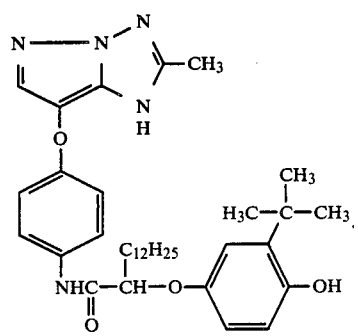 (24)
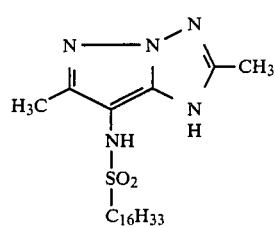 (25)
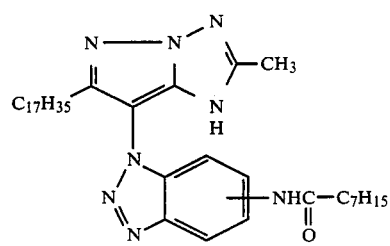 (26)

group capable of being released upon coupling which is bonded to the carbon atom of the coupling position through an oxygen atom, a nitrogen atom, a carbon atom or a sulfur atom.

4. A compound as claimed in claim 1, wherein $R_1$, $R_2$ or X are independently a divalent group for forming a bis coupler.

5. A compound as claimed in claim 2, wherein the aliphatic residue represented by $R_1$ or $R_2$ is a straight chain or branched chain alkyl group having from 1 to 32 carbon atoms, an aralkyl group, an alkenyl group, an alkinyl group or a cycloalkyl group and each of which may be substituted with a substituent bonded through an oxygen atom, a nitrogen atom, a sulfur atom or a carbonyl group, a hydroxy group, an amino group, a nitro group, a carboxy group, a cyano group or a halogen atom.

6. A compound as claimed in claim 3, wherein X represents a hydrogen atom, a halogen atom, a carboxy group, a group bonded to the coupling position through an oxygen atom, a group bonded to the coupling position through a nitrogen atom, a group bonded to the coupling position through a sulfur atom or a group bonded to the coupling position through a carbon atom.

7. A compound as claimed in claim 4, wherein the divalent group for forming a bis coupler represented by $R_1$ or $R_2$ is a substituted or unsubstituted alkenylene group, a substituted or unsubstituted phenylene group, a group of the formula —NHCO—$R_3$—CONH— (wherein $R_3$ represents a substituted or unsubstituted alkylene group or a subsituted or unsubstituted phenylene group) or a group of the formula —S—$R_3$—S— (wherein $R_3$ is the same meaning as defined above).

8. A compound as claimed in claim 1 is a compound represented by the general formula (I'):

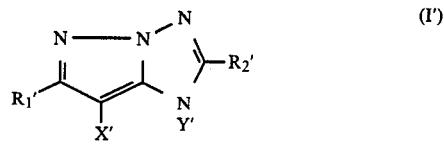

wherein $R_1'$ and $R_2'$ each independently represents a hydrogen atom, an alkyl group or a phenyl group; X' represents a hydrogen atom, a halogen atom, an acyl group, a nitroso group, an amino group, or a substituted amino group; and Y' represents a hydrogen atom or a benzyl group.

* * * * *